(12) United States Patent
Chen et al.

(10) Patent No.: US 10,186,667 B2
(45) Date of Patent: Jan. 22, 2019

(54) DIPHENYLIMIDAZOLE-FUSED, SPIRALLY CONFIGURED CIS-STILBENE/FLUORENE HYBRID COMPOUNDS AND ORGANIC LIGHT EMITTING DEVICE COMPRISING THE SAME

(71) Applicant: NICHEM FINE TECHNOLOGY CO., LTD., Jhubei, Hsinchu County (TW)

(72) Inventors: Chien-Tien Chen, Jhubei (TW); Chi-Chung Chen, Jhubei (TW)

(73) Assignee: NICHEM FINE TECHNOLOGY CO., LTD., Jhubei, Hsinchu County (TW)

( * ) Notice: Subject to any disclaimer, the term of this patent is extended or adjusted under 35 U.S.C. 154(b) by 125 days.

(21) Appl. No.: 15/228,600

(22) Filed: Aug. 4, 2016

(65) Prior Publication Data
US 2017/0040548 A1   Feb. 9, 2017

Related U.S. Application Data

(60) Provisional application No. 62/200,929, filed on Aug. 4, 2015.

(51) Int. Cl.
| | | |
|---|---|---|
| *H01L 51/54* | (2006.01) | |
| *C09K 11/06* | (2006.01) | |
| *H01L 51/00* | (2006.01) | |
| *C07D 235/02* | (2006.01) | |
| *C07D 403/14* | (2006.01) | |
| *C07D 401/14* | (2006.01) | |
| *C07C 255/52* | (2006.01) | |
| *C07F 9/53* | (2006.01) | |
| *C07C 211/58* | (2006.01) | |

(Continued)

(52) U.S. Cl.
CPC ........ *H01L 51/0072* (2013.01); *C07C 211/58* (2013.01); *C07C 255/52* (2013.01); *C07D 209/86* (2013.01); *C07D 213/06* (2013.01); *C07D 221/20* (2013.01); *C07D 235/02* (2013.01); *C07D 235/20* (2013.01); *C07D 251/24* (2013.01); *C07D 401/14* (2013.01); *C07D 403/14* (2013.01); *C07D 471/04* (2013.01); *C07D 471/10* (2013.01); *C07D 487/04* (2013.01); *C07F 5/027* (2013.01); *C07F 9/5329* (2013.01); *C09K 11/025* (2013.01); *C09K 11/06* (2013.01); *H01L 51/006* (2013.01); *H01L 51/008* (2013.01); *H01L 51/0052* (2013.01); *H01L 51/0056* (2013.01); *H01L 51/0058* (2013.01); *H01L 51/0061* (2013.01); *H01L 51/0067* (2013.01); *C07C 2603/32* (2017.05); *C09K 2211/1007* (2013.01); *C09K 2211/1014* (2013.01); *C09K 2211/1029* (2013.01); *C09K 2211/1044* (2013.01); *H01L 51/0096* (2013.01); *H01L 51/424* (2013.01); *H01L 51/44* (2013.01); *H01L 51/5056* (2013.01); *H01L 51/5072* (2013.01); *H01L 51/5096* (2013.01); *Y02E 10/549* (2013.01)

(58) Field of Classification Search
CPC .. C07D 235/00; C07D 235/02; C07D 235/20; C07D 209/86; C07D 213/00; C07D 213/02; C07D 213/06; C07D 401/00; C07D 401/14; C07D 403/00; C07D 403/14; C07D 251/00; C07D 251/24; C07D 471/00; C07D 471/04; C07D 471/10; C07D 487/00; C07D 487/04; C07D 487/10; C07D 211/58; C07C 255/52; C07C 2603/32; C09K 11/025; C09K 11/06; C09D 2211/00; C09D 2211/10; C09D 2211/1007; C09D 2211/1011; C09D 2211/1014; C09D 2211/1029; C09D 2211/1044; Y02E 10/549; C07F 5/027; C07F 9/5329; H01L 51/0032; H01L 51/005; H01L 51/0051; H01L 51/0052; H01L 51/0056; H01L 51/0059; H01L 51/0061; H01L 51/0062; H01L 51/0067; H01L 51/0071; H01L 51/0072; H01L 51/0073; H01L 51/0074; H01L 51/0095; H01L 51/44; H01L 51/424; H01L 51/50; H01L 51/5012; H01L 51/5016; H01L 51/5056; H01L 51/5072; H01L 51/5096
USPC ....... 428/690, 691, 917, 411.4, 336; 427/58, 427/66; 313/500–512; 257/40, 88–104, 257/E51.001–E51.052; 252/301.16–301.35
See application file for complete search history.

(56) References Cited

FOREIGN PATENT DOCUMENTS

CN          103936720 A  *  7/2014

OTHER PUBLICATIONS

Machine translation of CN103936720. (Year: 2014).*

* cited by examiner

*Primary Examiner* — Andrew K Bohaty
(74) *Attorney, Agent, or Firm* — Muncy, Geissler, Olds & Lowe, P.C.

(57) ABSTRACT

The present invention provides a series of diphenylimidazole-fused, spirally configured cis-stilbene/fluorene hybrid compounds and an optoelectronic device comprising the same. The diphenylimidazole-fused, spirally configured cis-stilbene/fluorene hybrid compound bearing cyanoaryl and cyanoheteroaryl substituents, and have glass transition temperatures ranged from 154° C. to 194° C., decomposition temperatures ranged from 426° C. to 443° C., reversible electron transport property, and balanced charges motilities. In addition, a variety of experimental data have proved that these diphenylimidazole-fused, spirally configured cis-stil- (Continued)

bene/fluorene hybrid materials can indeed be used as a hole-blocking type electron-transporter for phosphorescent OLEDs.

14 Claims, 1 Drawing Sheet

(51) Int. Cl.
*C07D 209/86* (2006.01)
*C07D 213/06* (2006.01)
*C07D 235/20* (2006.01)
*C07D 251/24* (2006.01)
*C07D 471/04* (2006.01)
*C07D 487/04* (2006.01)
*C07F 5/02* (2006.01)
*C09K 11/02* (2006.01)
*C07D 221/20* (2006.01)
*C07D 471/10* (2006.01)
*H01L 51/50* (2006.01)
*H01L 51/44* (2006.01)
*H01L 51/42* (2006.01)

DIPHENYLIMIDAZOLE-FUSED, SPIRALLY CONFIGURED CIS-STILBENE/FLUORENE HYBRID COMPOUNDS AND ORGANIC LIGHT EMITTING DEVICE COMPRISING THE SAME

CROSS REFERENCE TO RELATED APPLICATIONS

This patent application claims the benefit of U.S. Provisional Application No. 62/200,929, filed on Aug. 4, 2015, the content of which is hereby incorporated by reference in its entirety.

BACKGROUND OF THE INVENTION

Field of Invention

The present invention relates to the technology field of carrier transport and emitting materials, and more particularly to a series of spirally configured cis-stilbene/fluorene hybrid material as a hole-blocking type electron-transporters and emitters for OLEDs.

Related Art

It is well known that organic light emitting diode (OLED) was initially invented and proposed by Eastman Kodak Company through a vacuum evaporation method. Tang and VanSlyke of Kodak Company deposited an electron transport material such as $Alq_3$ on a transparent indium tin oxide (abbreviated as ITO) glass formed with an organic layer of aromatic diamine thereon, and subsequently completed the fabrication of an organic electroluminescent (EL) device after a metal electrode is vapor-deposited onto the $Alq_3$ layer. The organic EL device currently becomes a new generation lighting device or display because of high brightness, fast response speed, light weight, compactness, true color, no difference in viewing angles, without using any LCD backlight plates, and low power consumption.

Recently, some interlayers such as electron transport layer and hole transport layer are added between the cathode and the anode for increasing the current efficiency and power efficiency of the OLEDs. For example, an organic light emitting diode (OLED) 1' shown as FIG. 1 is designed to consist of: a cathode 11', an electron injection layer 13', a light emitting layer 14', a hole transport layer 16', and an anode 18'.

In device function concept, the light emitted by the OLED 1' is resulted from excitons produced by the recombination of electrons and holes in the light emitting layer 14'. However, according to theoretical speculation, the ratio of the excitons with singlet excited state and the excitons with triplet excited state is 3:1. So that, when a small molecular fluorescent material is used as the light-emitting layer 14' of the OLED 1', there are about 25% excitons being used in emitting light, and the rest of 75% excitons with triplet excited state are lost through non-luminescence mechanism. For this reason, the general fluorescent material performs a maximum quantum yield of 25% in limit which amounts to an external quantum efficiency of 5% in the device.

Moreover, researches further find that certain hole transport material can simultaneously perform electron confining ability, such as the material represented by following chemical formulas 1' and 2'. The chemical formula 1' represents the chemical structure of Tris(4-carbazoyl-9-ylphenyl) amine, which is called TCTA in abbreviation. The chemical formula 2' represents the chemical structure of N,N'-Di(1-naphthyl)-N,N'-diphenyl-(1,1'-biphenyl)-4,4'-diamine called NPB in abbreviation.

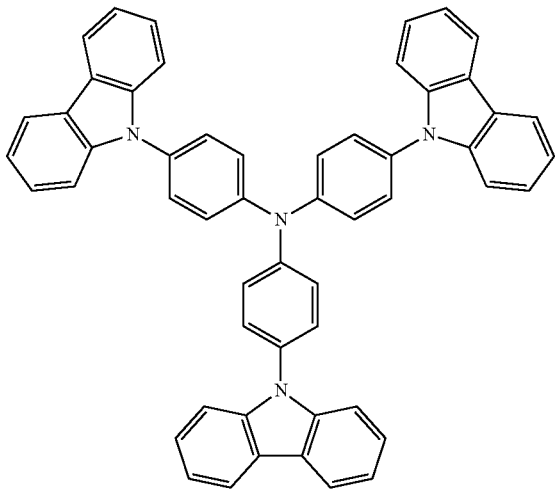

[chemical formula 1']

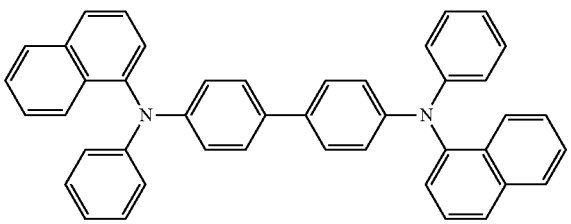

[chemical formula 2']

Recently, for effectively increasing the lighting performance of OLEDs, OLED manufactures and researchers have made great efforts to develop electron transport materials with hole blocking functionality, such as TmPyPb, TPBi, 3TPYMB, BmPyPb, and DPyPA represented by following chemical formula 3'-7', respectively. Wherein TmPyPb is the abbreviation of 3,3'-[5'-[3-(3-Pyridinyl)phenyl][1,1':3',1''-terphenyl]-3,3''-diyl]bispyridine, TPBi is the abbreviation of 1,3,5-Tris(1-phenyl-1H-benzimidazol-2-yl)benzene, 3TPYMB is the abbreviation of Tris(2,4,6-triMethyl-3-(pyridin-3-yl)phenyl)borane, BmPyPb is the abbreviation of 1,3-bis(3,5-dipyrid-3-yl-phenyl)benzene, and DPyPA is the abbreviation of 9,10-bis(3-(pyridin-3-yl)phenyl) anthracene.

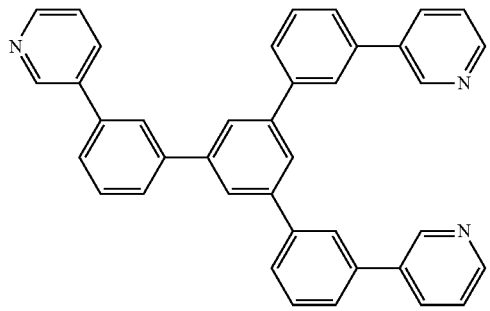

[chemical formula 3']

-continued

[chemical formula 4']

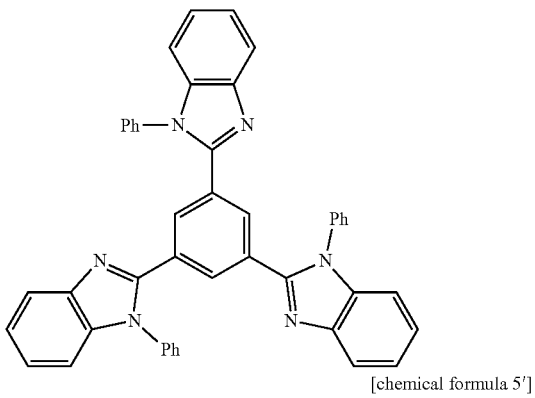

[chemical formula 5']

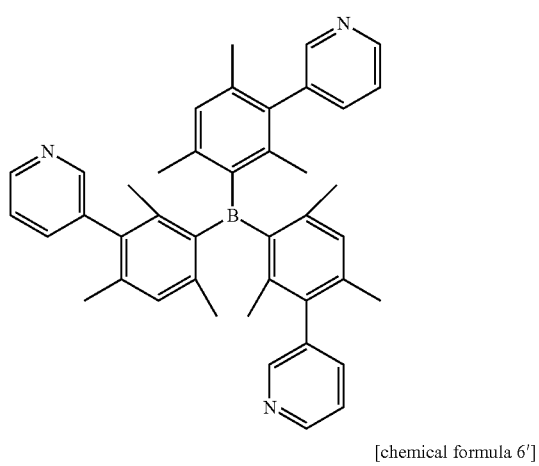

[chemical formula 6']

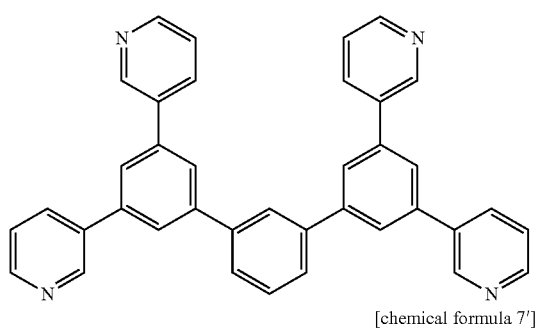

[chemical formula 7']

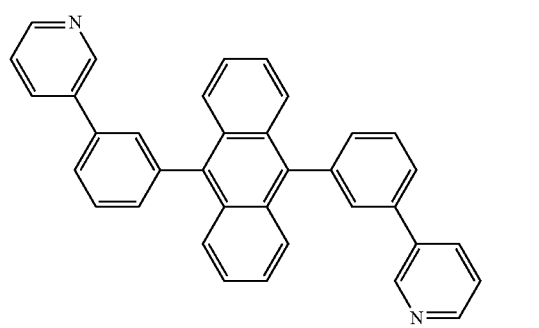

In spite of various electron transport materials with hole blocking functionality have been developed, the phosphorescence OLEDs applied with the said electron transport materials still cannot perform outstanding luminous efficiency and device lifetime. Accordingly, in view of the conventional or commercial electron transport materials with hole blocking functionality still including drawbacks, the inventor of the present application has made great efforts to make inventive research thereon and eventually provided a series of diphenylimidazole-fused, spirally configured cis-stilbene/fluorene hybrid materials bearing cyanoaryl and cyano-heteroaryl subunits as hole-blocking type electron-transporters and emitters for OLED.

SUMMARY OF THE INVENTION

An aspect of the disclosure is to provide a series of diphenylimidazole-fused, spirally configured cis-stilbene/fluorene hybrid compounds bearing cyanoaryl and cyano-heteroaryl subunits, which are diphenylimidazole-fused, spirally-configured cis-stilbene/fluorene derivatives having glass transition temperatures ranged from 154° C. to 194° C., decomposition temperatures ranged from 426° C. to 443° C., reversible electron transport property, and balanced charges motilities. In addition, a variety of experimental data have proved that these diphenylimidazole-fused, spirally configured cis-stilbene/fluorene hybrid materials can indeed be used as hole-blocking type, electron-transporters and emitting materials for OLEDs.

Therefore, one objective of the present invention is to provide a compound which comprises a seven-membered ring portion and an imidazole fragment. The seven-membered ring portion is composed of a cis-stilbene fragment and a tetrahedral coordination bridging atom fragment, and the imidazole fragment is connected to the cis-stilbene fragment.

Another objective of the present invention is to provide an optoelectronic device comprising a first electrode, an interlayer and a second electrode sequentially disposed on a substrate, wherein the interlayer has a compound. The compound comprises a seven-membered ring portion and an imidazole fragment. The seven-membered ring portion is composed of a cis-stilbene fragment and a tetrahedral coordination bridging atom fragment, and the imidazole fragment is connected to the cis-stilbene fragment.

In one embodiment, the tetrahedral coordination bridging atom fragment is selected from the groups of general formulas I-1-1 to I-1-4.

(general formula I-1-1)

(general formula I-1-2)

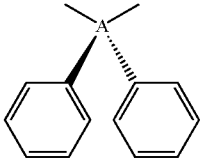

(general formula I-1-3)

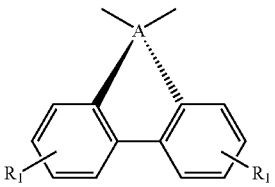

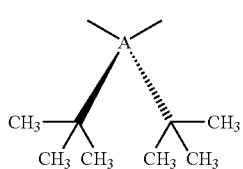
(general formula I-1-4)

A is carbon atom or silicon atom, $R_1$ is a hydrogen atom, tert-butyl group or naphthyl group.

In one embodiment, the seven-membered ring portion and/or the imidazole fragment has at least one substituent, the substituent is independently a halogen atom, cyano group, substituted or unsubstituted trifluoromethyl group, phosphine oxide group, amine group, aromatic ring group, heteroaromatic ring group, alkyl group or alkenyl group.

In one embodiment, the compound is applied in an organic light emitting device (OLED) for being as a hole-blocking material, an electron-transporting material and/or a light emitting material.

In one embodiment, the compound is represented by general formula I:

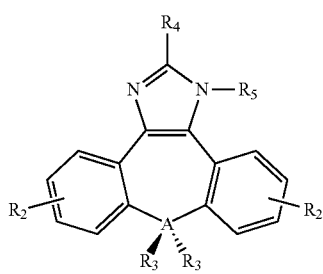
(general formula I)

A is carbon atom or silicon atom. $R_2$ is independently a hydrogen atom, phosphine oxide group, amine group, aromatic ring group, heteroaromatic ring group, alkyl group or alkenyl group optionally substituted by one or more radicals Y. $R_4$ and $R_5$ are identical or different and each of $R_4$ and $R_5$ is independently an aromatic ring group, heteroaromatic ring group, alkyl group or alkenyl group optionally substituted by one or more radicals Y The radical Y is identical or different on each occurrence and is a hydrogen atom, halogen atom, cyano group, trifluoromethyl group, phosphine oxide group, alkyl group, alkenyl group, aromatic ring group or heteroaromatic ring group optionally substituted by one or more radicals Y. The radical Y' is identical or different on each occurrence and is a hydrogen atom, cyano group, diphenylamine group, aromatic ring group, heteroaromatic ring group, alkyl group or alkenyl group. $R_3$ is independently a methyl group, phenyl group, tert-butyl group or two of $R_3$ are linked by a single bond represented by general formula I-2.

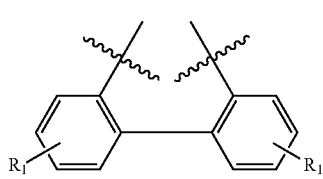
(general formula I-2)

$R_1$ is a hydrogen atom, tert-butyl group or naphthyl group.

In one embodiment, the aromatic ring group or heteroaromatic ring group in $R_2$, $R_4$, $R_5$, Y or Y' is independently a fused aryl group or heteroaryl group.

In one embodiment, the aromatic ring group or heteroaromatic ring group in $R_2$, $R_4$, $R_5$ or Y is independently a phenyl group, 1-naphthyl group, 2-naphthyl group, thiophenyl group, pyrimidinyl group, pyrrolyl group, quinolinyl group, triazinyl group, pyridyl group or benzimidazolyl group.

In one embodiment, the aromatic ring group or heteroaromatic ring group in $R_2$, $R_4$, $R_5$ or Y' is independently an imidazolyl group, phenyl group, pyridyl group, 1H-pyrrolo[2,3-b]pyridine group or carbazolyl group.

In one embodiment, the alkyl group or alkenyl group in $R_2$, $R_4$, $R_5$, Y or Y' is independently a straight-chain alkyl group or alkenyl group, a branched alkyl group or alkenyl group, or a cyclic alkyl group or alkenyl group.

In one embodiment, $R_2$ is selected from the group consisting of general formula II-1-1 to general formula II-1-57, and wherein n is 1 or 2.

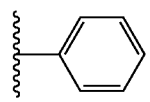
general formula II-1-1

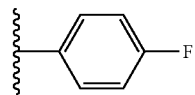
general formula II-1-2

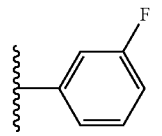
general formula II-1-3

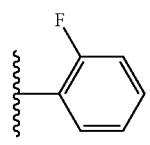
general formula II-1-4

general formula II-1-5

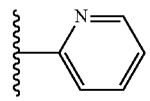
general formula II-1-6

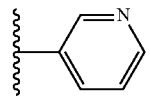
general formula II-1-7

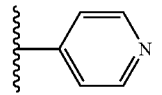
general formula II-1-8

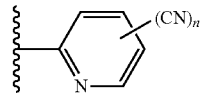
general formula II-1-9

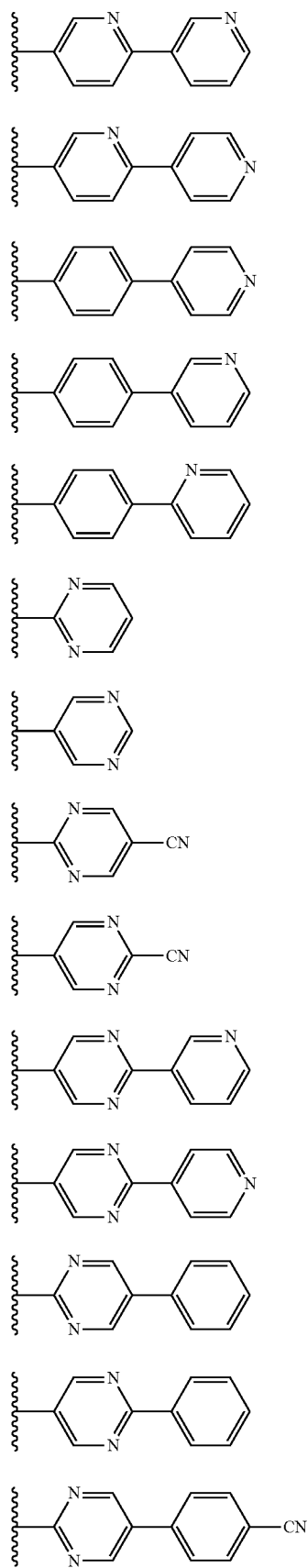
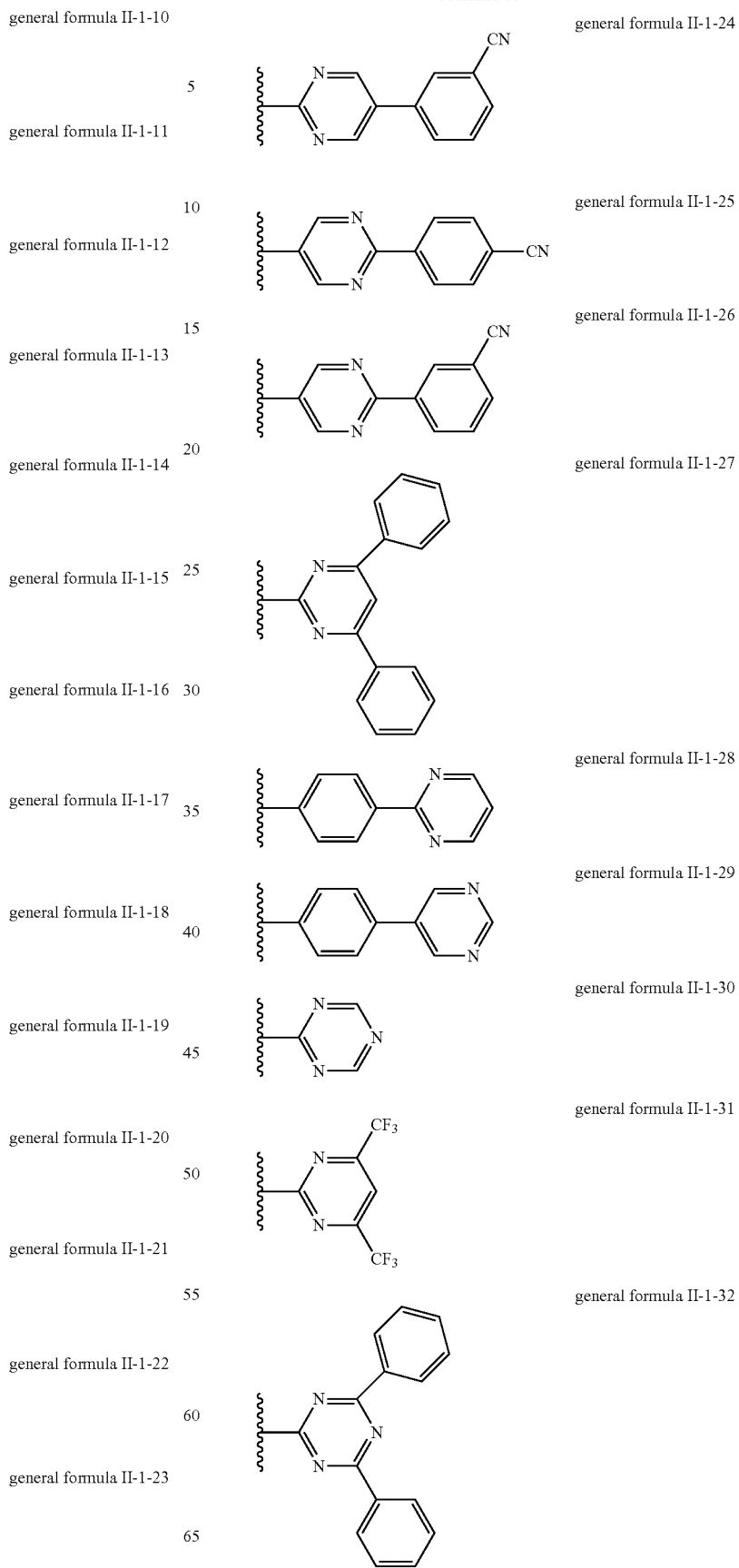

general formula II-1-33
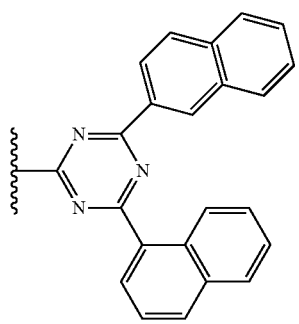
general formula II-1-34
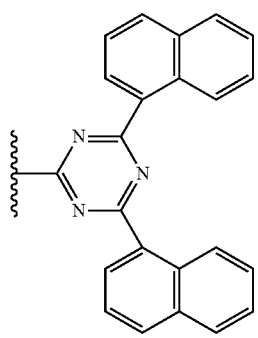
general formula II-1-35
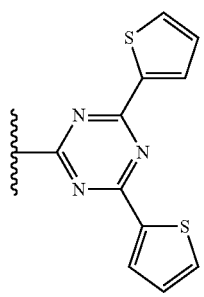
general formula II-1-36
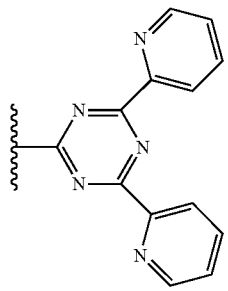
general formula II-1-37
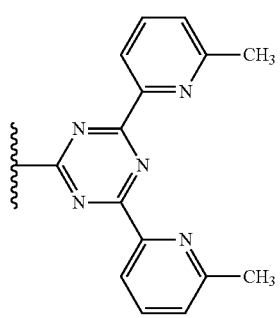
general formula II-1-38
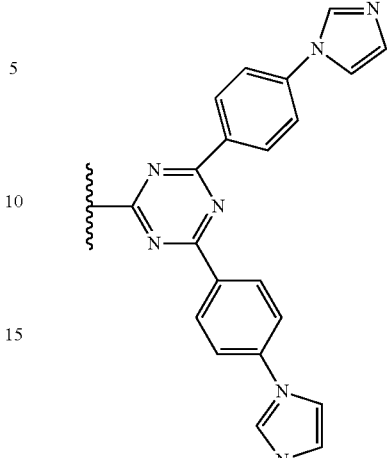
general formula II-1-39
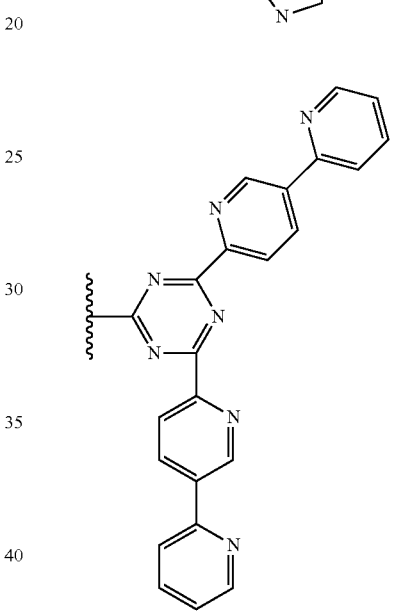
general formula II-1-40
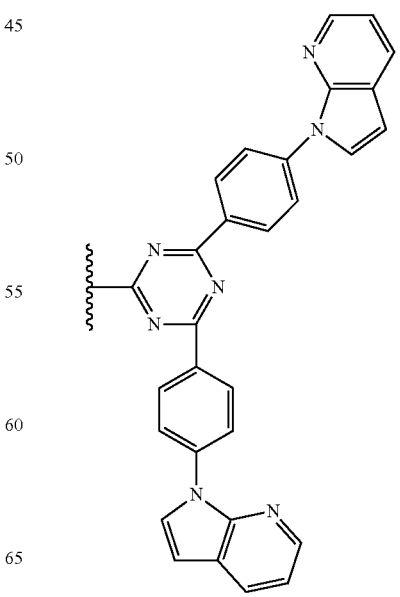

-continued
general formula II-1-41
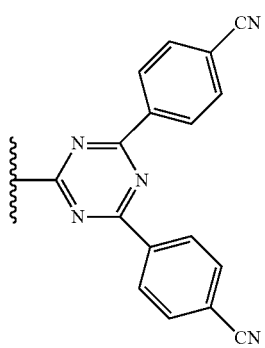
general formula II-1-42
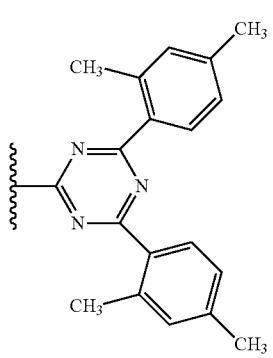
general formula II-1-43
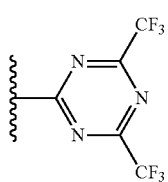
general formula II-1-44
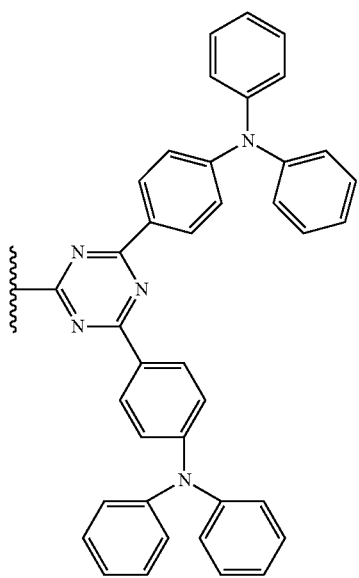
-continued
general formula II-1-45
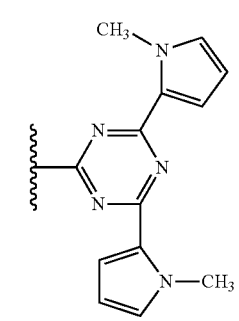
general formula II-1-46
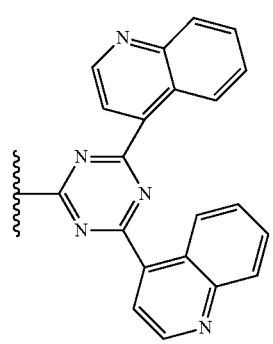
general formula II-1-47
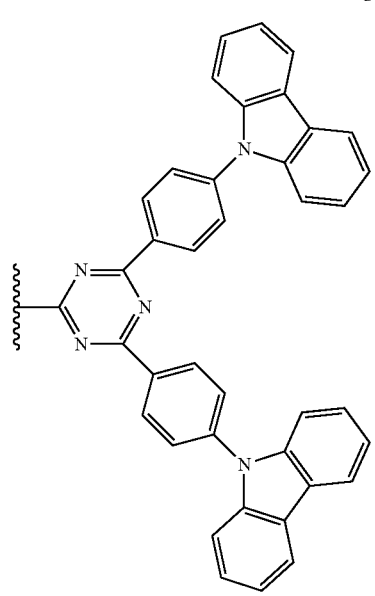
general formula II-1-48
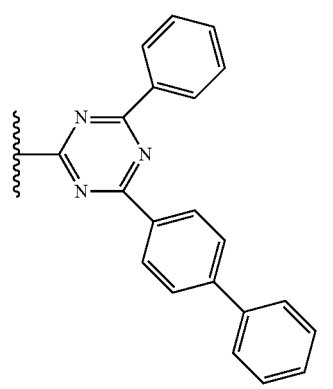

general formula II-1-49

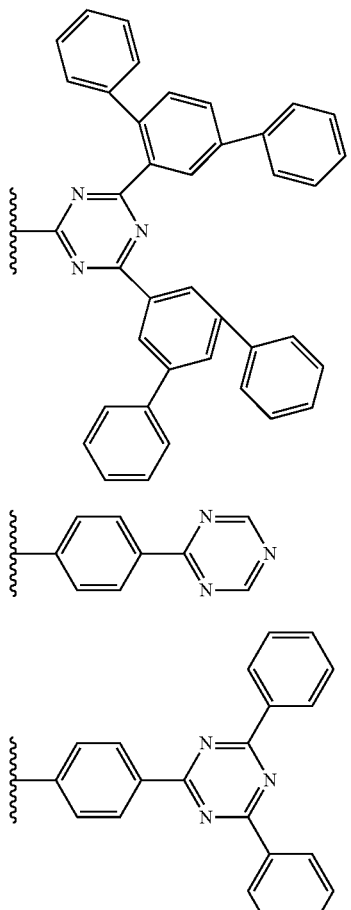

general formula II-1-50 general formula II-1-51 general formula II-1-52 general formula II-1-53

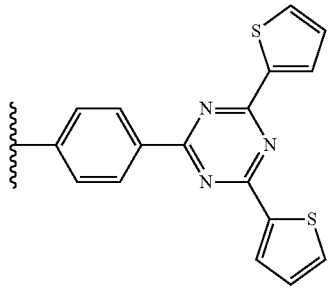

general formula II-1-54

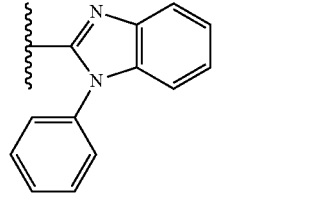

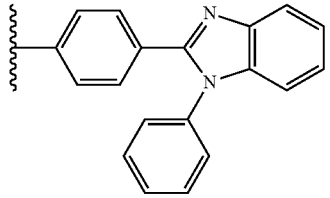

general formula II-1-55

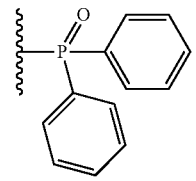

general formula II-1-56

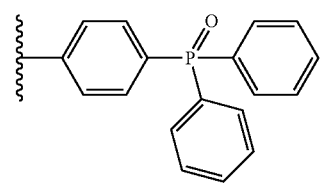

general formula II-1-57

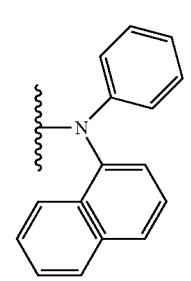
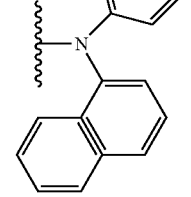

In one embodiment, the optoelectronic device is an organic light emitting device (OLED), the interlayer is an electron transport layer, a hole blocking layer and/or a light emitting layer.

Another objective of the present invention is to provide a process for the synthesis of a compound of chemical formula B. The process comprises the following step: reacting a compound of chemical formula B-1 and a compound of chemical formula B-2 to produce the compound of chemical formula B.

chemical formula B

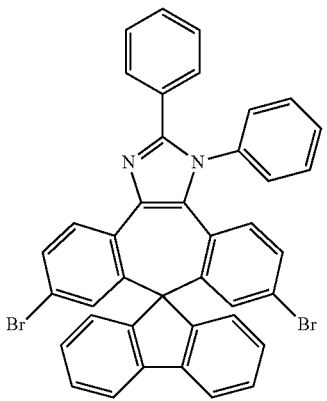

chemical formula B-1

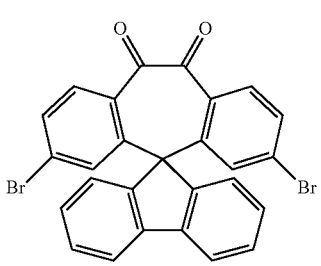

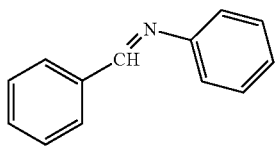

chemical formula B-2

As mentioned above, as to the series of diphenylimidazole-fused, spirally configured cis-stilbene/fluorene hybrid compounds and the optoelectronic device comprising the same according to the disclosure, the compounds bear cyanoaryl and cyano-heteroaryl subunits, and are diphenylimidazole-fused, spirally-configured cis-stilbene/fluorene derivatives having glass transition temperatures ranged from 154° C. to 194° C., decomposition temperatures ranged from 426° C. to 443° C., reversible electron transport property, and balanced charges motilities. In addition, a variety of experimental data have proved that these diphenylimidazole-fused, spirally configured cis-stilbene/fluorene hybrid materials can indeed be used as hole-blocking type, electron-transporters and emitting materials for OLEDs. Moreover, the experimental data also reveal that the OLEDs using these diphenylimidazole-fused, spirally configured cis-stilbene/fluorene hybrid materials can indeed be used as the hole-blocking type electron-transporters and are able to show excellent external quantum efficiency ($\eta_{ext}$), current efficiency ($\eta_c$), power efficiency ($\eta_p$), maximum luminance ($L_{max}$), and device lifetime better than those of phosphorescent OLEDs based on the conventional or commercial electron transport materials.

BRIEF DESCRIPTION OF THE DRAWINGS

The invention will become more fully understood from the detailed description and accompanying drawings, which are given for illustration only, and thus are not limitative of the present invention, and wherein.

DETAILED DESCRIPTION OF THE INVENTION

Figure 1:
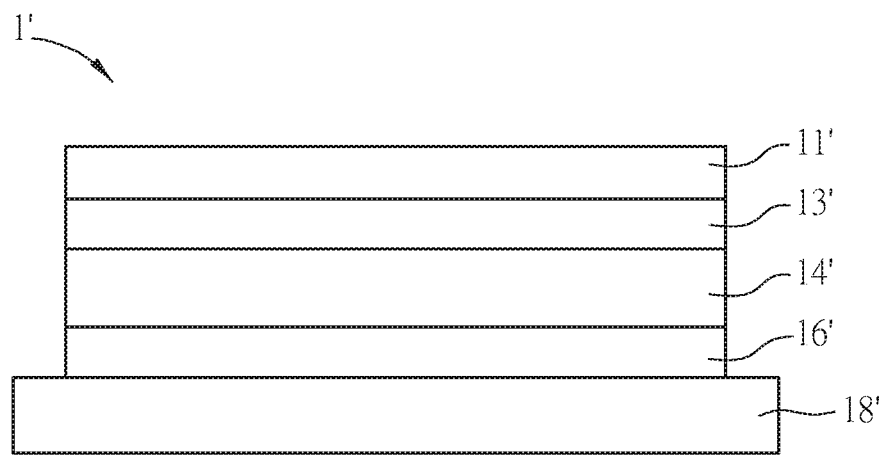
FIG. 1 is a schematic diagrams showing a conventional organic light emitting diode (OLED)

The embodiments of the invention will be apparent from the following detailed description, which proceeds with reference to the accompanying drawings, wherein the same references relate to the same elements.

The present invention provides a series of diphenylimidazole-fused, spirally configured cis-stilbene/fluorene hybrid compounds bearing cyanoaryl and cyano-heteroaryl subunits for OLEDs. These diphenylimidazole-fused, spirally configured cis-stilbene/fluorene hybrid compounds, constructed by at least one diphenylimidazole-fused, cis-stilbene based component and at least one fluorene based component, are diphenylimidazole-fused, spirally-configured cis-stilbene/fluorene derivatives having the functions to block holes. These diphenylimidazole-fused, spirally configured cis-stilbene/fluorene hybrid compounds are mainly applied in OLEDs for being as an electron transport layer and/or a hole blocking layer. Moreover, these diphenylimidazole-fused, spirally configured cis-stilbene/fluorene hybrid compounds can also be applied in a solar cell for being as a carrier transport layer.

According to one of the preferred embodiments of the present invention, a compound comprises a seven-membered ring portion and an imidazole fragment. As described above, the compound can be applied in an organic light emitting device (OLED) for being as a hole-blocking material, an electron-transporting material and/or a light emitting material. The seven-membered ring portion is composed of a cis-stilbene fragment and a tetrahedral coordination bridging atom fragment, and the imidazole fragment is connected to the cis-stilbene fragment. In addition, the seven-membered ring portion and/or the imidazole fragment preferably have at least one substituent, and the substituent is independently a halogen atom, cyano group, substituted or unsubstituted trifluoromethyl group, phosphine oxide group, amine group, aromatic ring group, heteroaromatic ring group, alkyl group or alkenyl group. The tetrahedral coordination bridging atom fragment is selected from the groups of general formulas I-1-1 to I-1-4.

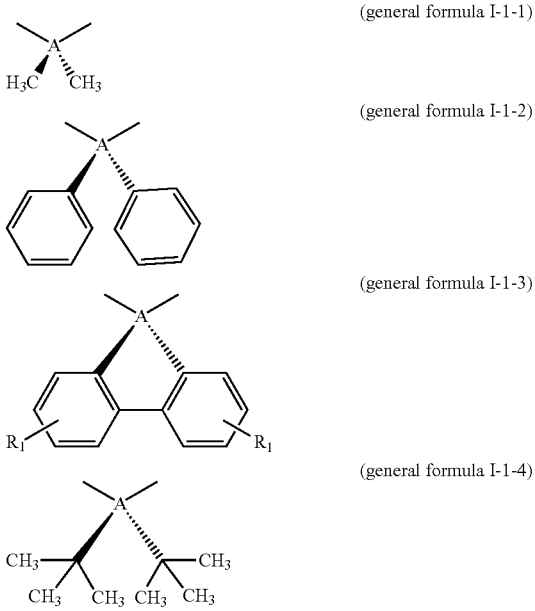

(general formula I-1-1)

(general formula I-1-2)

(general formula I-1-3)

(general formula I-1-4)

A is carbon atom or silicon atom. $R_1$ is a hydrogen atom, tert-butyl group or naphthyl group.

In one of the preferred embodiments of the present invention, the aforementioned diphenylimidazole-fused, spirally configured cis-stilbene/fluorene hybrid compound can be represented by general formula I:

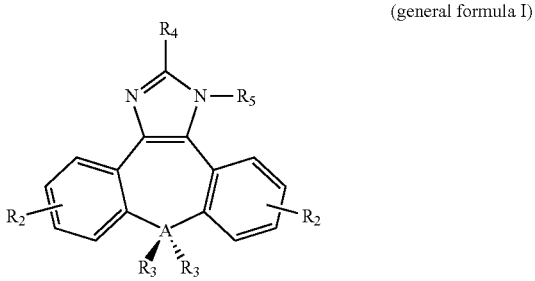

(general formula I)

A is carbon atom or silicon atom. $R_2$ is independently a hydrogen atom, phosphine oxide group, amine group, aromatic ring group, heteroaromatic ring group, alkyl group or alkenyl group optionally substituted by one or more radicals Y. $R_4$ and $R_5$ are identical or different and each of $R_4$ and $R_5$ is independently an aromatic ring group, heteroaromatic ring group, alkyl group or alkenyl group optionally substituted by one or more radicals Y. The radical Y is identical or different on each occurrence and is a hydrogen atom, halogen atom, cyano group, trifluoromethyl group, phosphine oxide group, alkyl group, alkenyl group, aromatic ring group or heteroaromatic ring group optionally substituted by one or more radicals Y The radical Y' is identical or different on each occurrence and is a hydrogen atom, cyano group, diphenylamine group, aromatic ring group, heteroaromatic ring group, alkyl group or alkenyl group. $R_3$ is independently a methyl group, phenyl group, tert-butyl group or two of $R_3$ are linked by a single bond represented by general formula I-2.

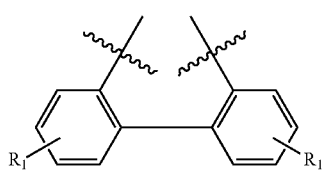

(general formula I-2)

$R_1$ is a hydrogen atom, tert-butyl group or naphthyl group.

In addition, the aromatic ring group or heteroaromatic ring group in $R_2$, $R_4$, $R_5$, Y or Y' is independently a fused aryl group or heteroaryl group. The aromatic ring group or heteroaromatic ring group in $R_2$, $R_4$, $R_5$ or Y is independently a phenyl group, 1-naphthyl group, 2-naphthyl group, thiophenyl group, pyrimidinyl group, pyrrolyl group, quinolinyl group, triazinyl group, pyridyl group or benzimidazolyl group. In detail, the aromatic ring group or heteroaromatic ring group in $R_2$, $R_4$, $R_5$ or Y' is independently an imidazolyl group, phenyl group, pyridyl group, 1H-pyrrolo[2,3-b]pyridine group or carbazolyl group.

In one of the preferred embodiments of the present invention, the alkyl group or alkenyl group in $R_2$, $R_4$, $R_5$, Y or Y' is independently a straight-chain alkyl group or alkenyl group, a branched alkyl group or alkenyl group, or a cyclic alkyl group or alkenyl group.

In detail, $R_2$ can be any one of the radical which is selected from the group consisting of general formula II-1-1 to general formula II-1-57, and n is 1 or 2.

general formula II-1-1

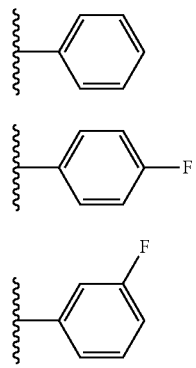

general formula II-1-2 general formula II-1-3 general formula II-1-4

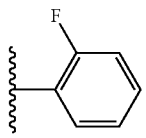

general formula II-1-5

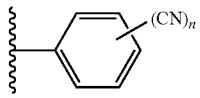

general formula II-1-1=6

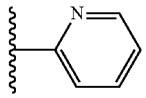

general formula II-1-7

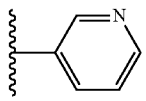

general formula II-1-8

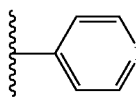

general formula II-1-9

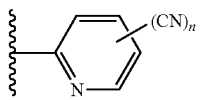

general formula II-1-10

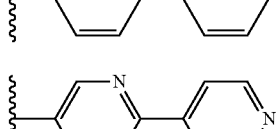

general formula II-1-11

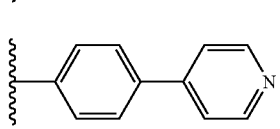

general formula II-1-12

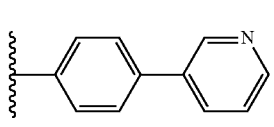

general formula II-1-13

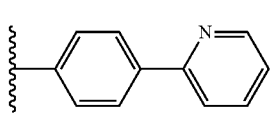

general formula II-1-14

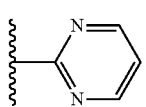

general formula II-1-15

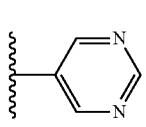

general formula II-1-16 general formula II-1-17

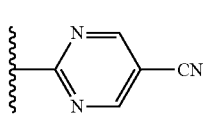

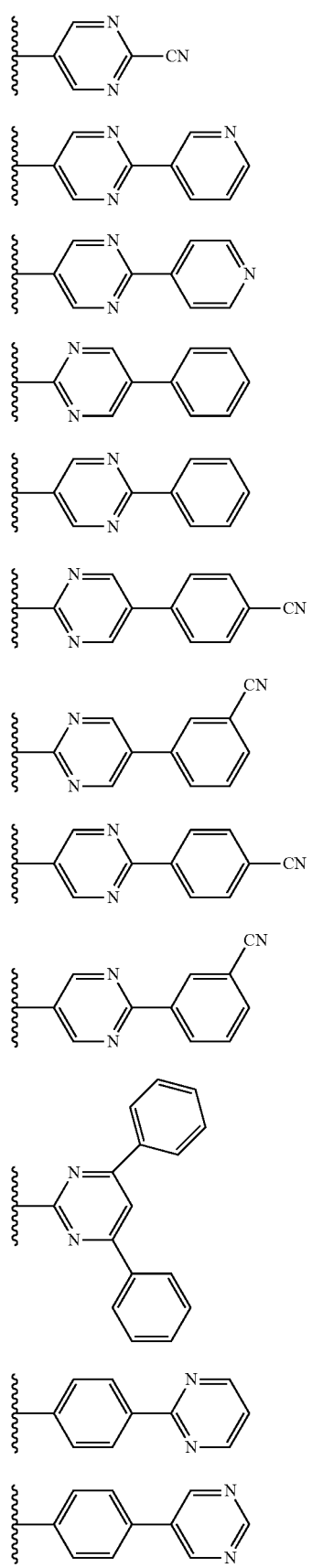
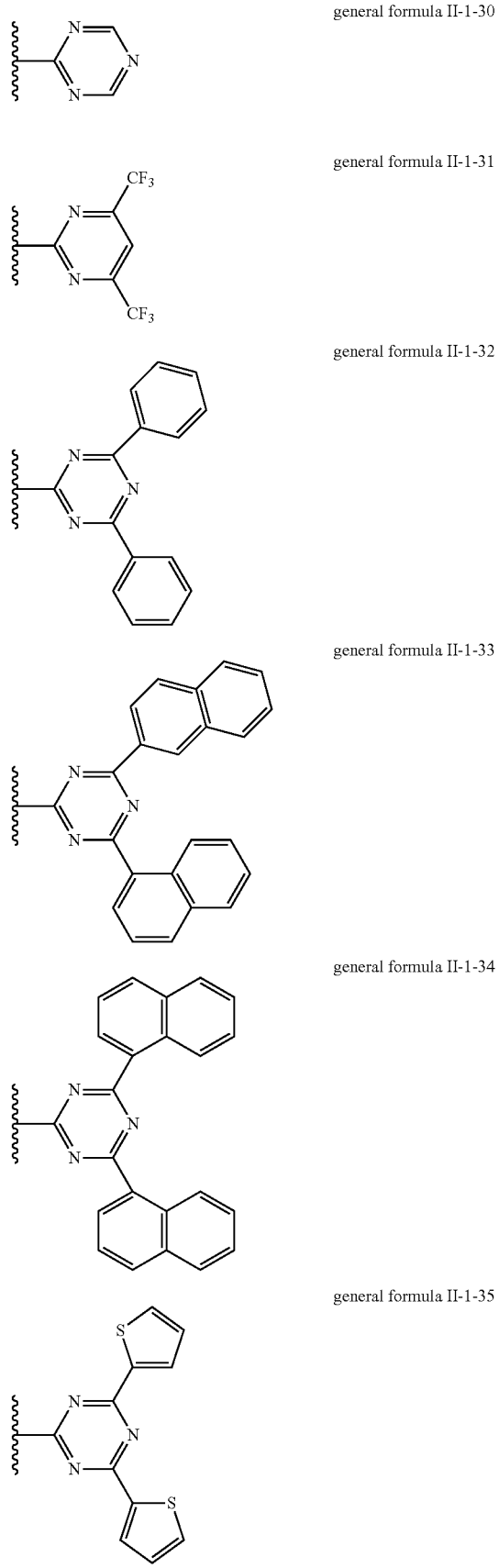
general formula II-1-18
general formula II-1-19
general formula II-1-20
general formula II-1-21
general formula II-1-22
general formula II-1-23
general formula II-1-24
general formula II-1-25
general formula II-1-26
general formula II-1-27
general formula II-1-28
general formula II-1-29
general formula II-1-30
general formula II-1-31
general formula II-1-32
general formula II-1-33
general formula II-1-34
general formula II-1-35

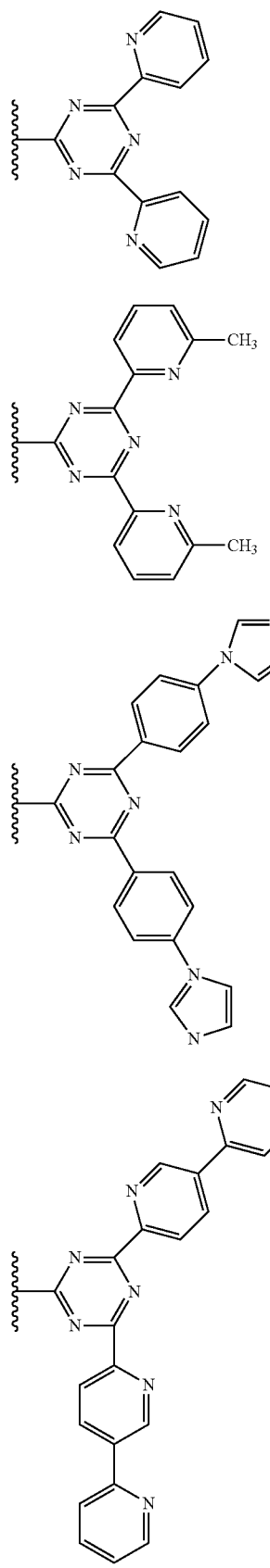
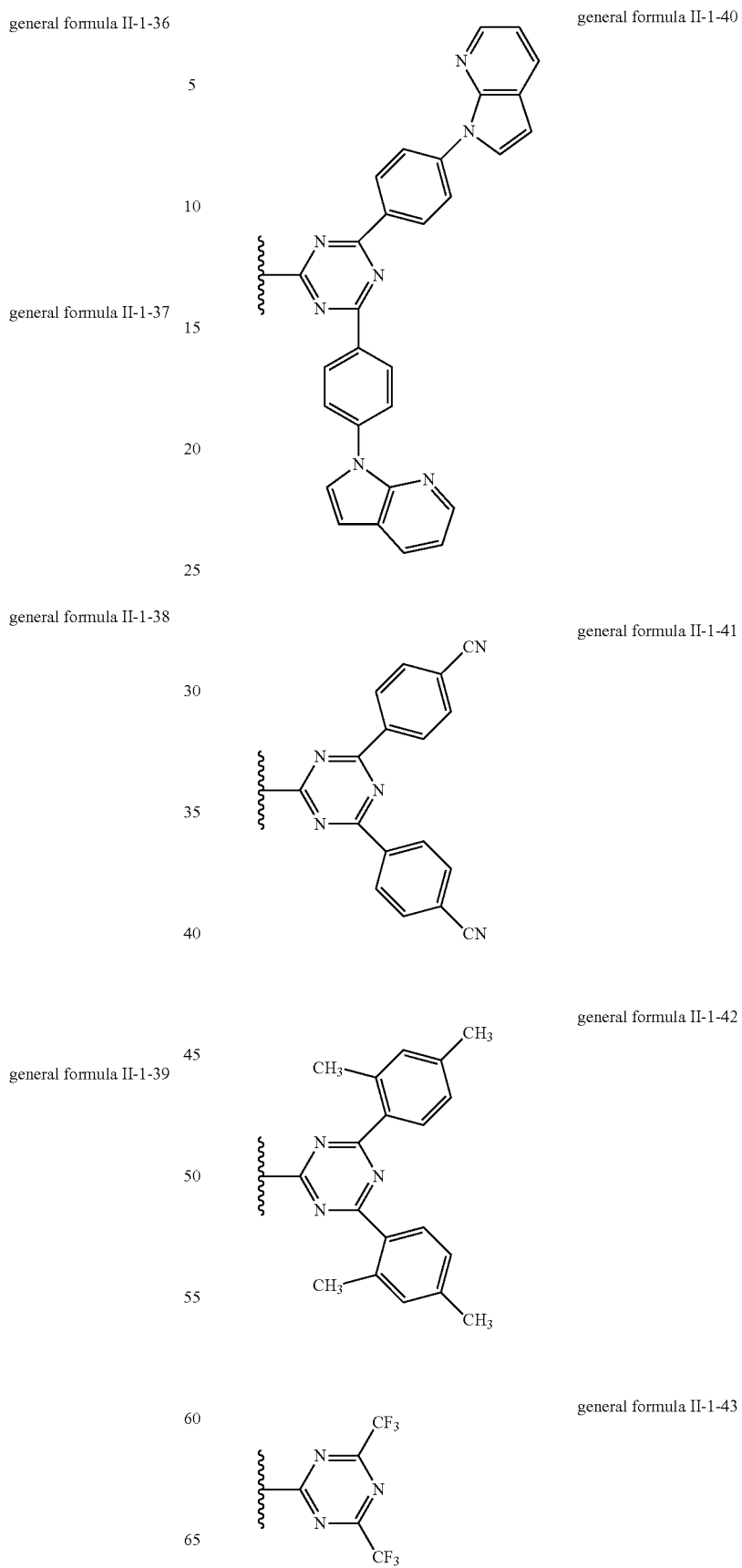

general formula II-1-44
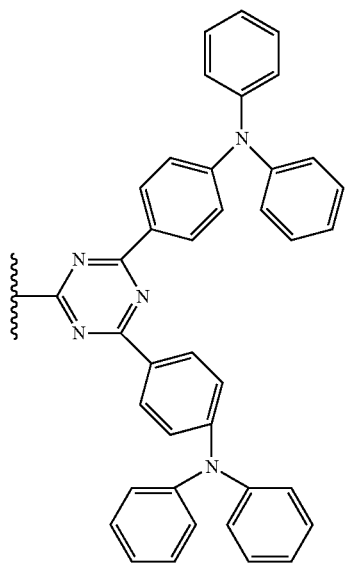
general formula II-1-45
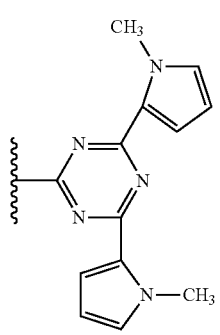
general formula II-1-46
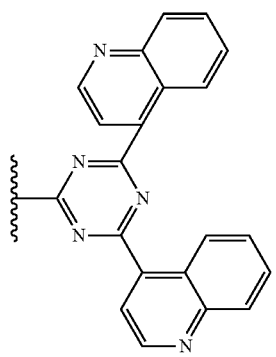
general formula II-1-47
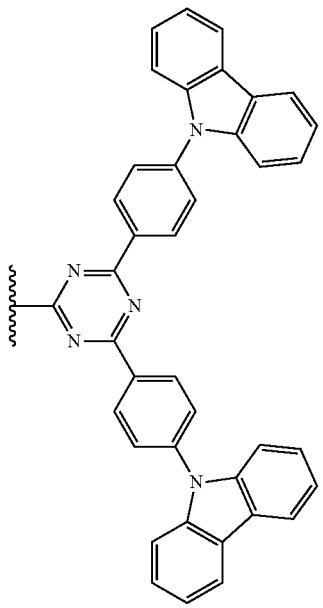
general formula II-1-48
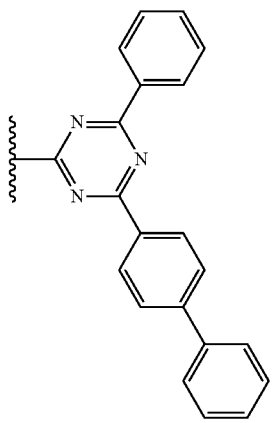
general formula II-1-49
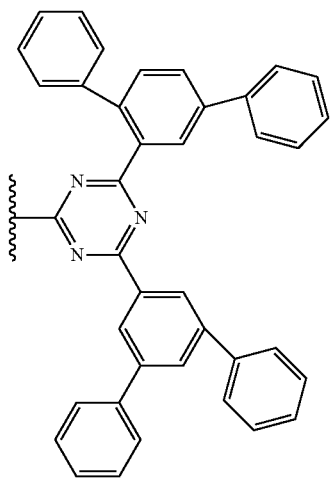
general formula II-1-50
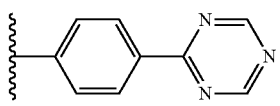

general formula II-1-51
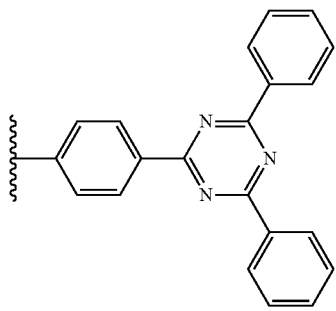

general formula II-1-52
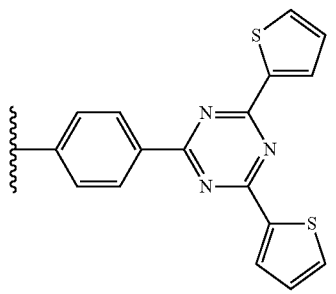

general formula II-1-53
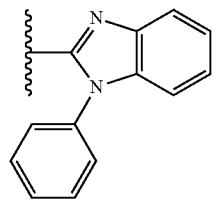

general formula II-1-54
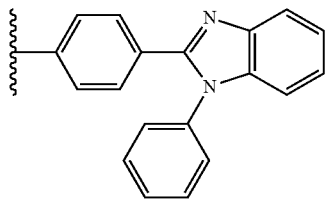

general formula II-1-55
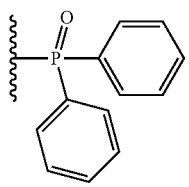

general formula II-1-56
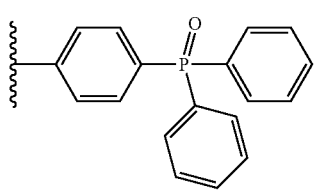

general formula II-1-57
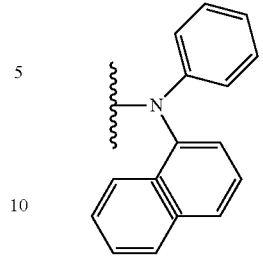

To manufacture the said diphenylimidazole-fused, spirally configured cis-stilbene/fluorene hybrid materials of the present invention, a key intermediate product needs to be firstly fabricated by using following steps:

(1) dissolving 30 mM 2-bromobiphenyl of 5.2 mL in 100 mL of anhydrous tetrahydrofuran (THF);

(2) placing the solution obtained from the step (1) in an environment of −78° C. for standing;

(3) taking 12 mL of n-butyllithium in hexanes solution (30 mM) from a n-butyllithium solution 2.5 M in hexanes, and then adding the 12 mL n-butyllithium hexanes solution dropwise into the solution obtained from the step (2) and stirring for 30 min (4) dissolving 20 mM diphenylimidazole-fused, 3,7-dibromo-dibenzosuberenone of 11.13 g in 60 mL of anhydrous THF;

(5) adding the solution obtained from step (4) to the reaction mixture in step (3) dropwise;

(6) adding 10 mL of saturated aqueous sodium bicarbonate solution into the product obtained from the step (5) for executing a quenching reaction, and then remove the THF by rotary evaporation;

(7) treating the product obtained from the step (6) with a extracting process by using dichloromethane, and then obtaining an extract liquid extract;

(8) adding 5 g magnesium sulfate into the extract liquid extract, and then treat a drying process and a filtering process to the liquid extract sequentially; and (9) using a rotary evaporating process to the product obtained from the step (8), so as to obtain a an intermediate product.

Furthermore, the following steps can be used for making another intermediate product of clear crystalline material.

(10) dissolving the intermediate product from step (9) in 60 mL acetic acid;

(11) adding 1 mL of concentrated hydrochloric acid (12 N) into the solution obtained from the step (10);

(12) letting the solution mixture obtained from the step (11) to react for 2 hours at 120° C. by using a reflux device;

(13) cooling the temperature of the product obtained from the step (12) down to 0° C.;

(14) adding 60 mL hexane into the product obtained from the step (13);

(15) using a Buchner funnel to treat the product obtained from the step (14) with a filtering process, so as to obtain a precipitate;

(16) using hexane to wash the precipitate for 3 times, so as to obtain a solid material;

(17) using dichloromethane/hexane to treat the solid with a recrystallization process for obtaining a clear crystal solid, wherein the clear crystal solid is presented by following chemical formula 1.

[chemical formula 1]

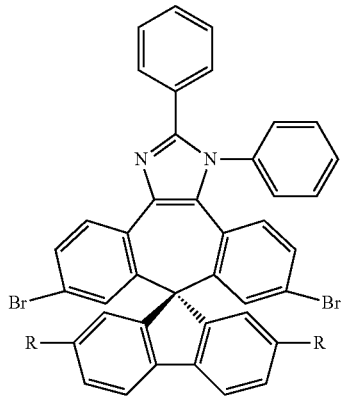

Spectral data for chemical formula 1: (R=H): m.p. 322.11° C. (DSC); M.W.: 690.03; $^1$H NMR (500 MHz, CDCl$_3$) 8.31 (d, J=8.3, 1H), 7.82 (d, J=7.8, 2H), 7.51 (dd, J=8.4, 1.9, 1H), 7.46 (m, 4H), 7.34 (m, 8H), 7.19 (d, J=2.0, 1H), 7.04 (s, 2H), 6.93 (dd, J=8.4, 2.0, 1H), 6.60 (d, J=8.4, 1H); $^{13}$C NMR (125 MHz, CDCl$_3$) 148.96, 144.72, 143.22, 136.93, 132.27, 131.66, 130.92, 130.82, 130.49, 130.20, 129.86, 129.50, 129.30, 128.86, 128.71, 128.24, 127.54, 127.29, 121.96, 121.73, 120.71, 65.85; HR-MS calcd for $C_{40}H_{24}Br_2N_2$: 690.0306. found: 690.0309. Anal. Calcd for $C_{40}H_{24}Br_2N_2$: C, 69.38; H, 3.49; N, 4.05. found: C, 68.97; H, 3.62; N, 3.97. TLC R$_f$ 0.21 (EtOAc/hexane, 1/8).

Furthermore, various exemplary embodiments for the diphenylimidazole-fused, spirally configured cis-stilbene/fluorene hybrid compounds of the present invention can be fabricated by treating certain chemical reaction method to the key intermediate product of clear crystalline materials represented by the chemical formula 1, such as Suzuki coupling reactions. Therefore, the exemplary embodiments of these diphenylimidazole-fused, spirally configured cis-stilbene/fluorene hybrid materials are represented by following chemical formula 2, chemical formula 3, chemical formula 4, and chemical formula 5:

[chemical formula 2]

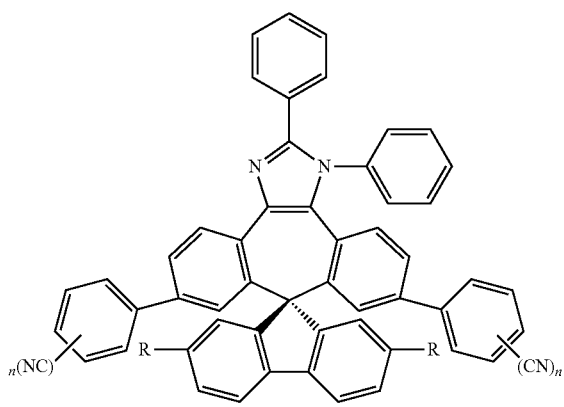

[chemical formula 3]

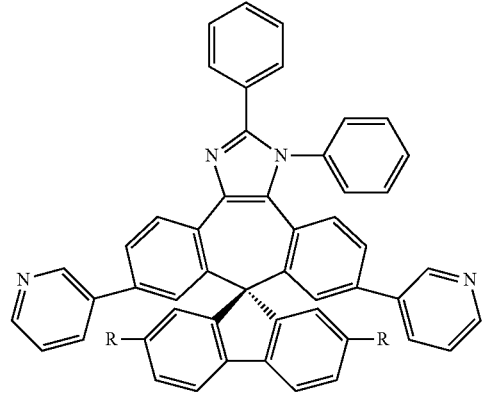

[chemical formula 4]

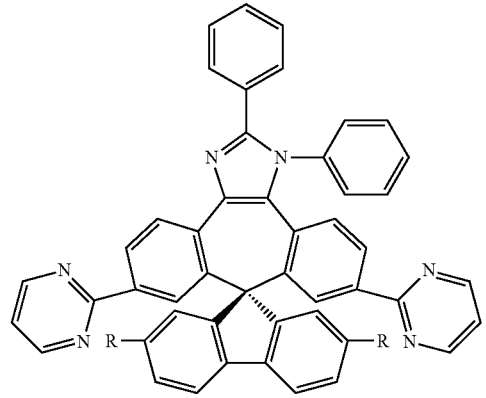

[chemical formula 5]

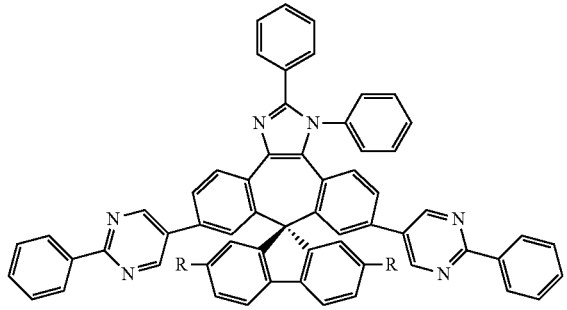

In the above-presented chemical formulas, R can be hydrogen group or tert-butyl group, and n can be 1 or 2. Representative spectroscopic data of chemical formula 2 (n=1): T$_m$ 326° C. (DSC); T$_g$: 194° C.; M.W.: 736.88; $^1$H NMR (400 MHz, CDCl$_3$) δ 8.55 (d, J=8.0 Hz, 1H), 7.81 (d, J=7.4 Hz, 2H), 7.63-7.49 (m, 10H), 7.46-7.31 (m, 15H), 7.24 (d, J=1.8 Hz, 2H), 7.10 (d, J=6 Hz, 2H), 7.05 (d, J=8.0 Hz, 1H), 6.86 (dd, J=8.0 Hz, J=1.4 Hz, 1H); TLC R$_f$ 0.32 (ethyl acetate/hexanes, 3/1); HRMS calcd for $C_{54}H_{32}N_4$: 736.2627. found: 736.2633.

Data for the compound of the formula 4: T$_m$ 338° C. (DSC); M.W.: 690.81; $^1$H NMR (400 MHz, CDCl$_3$) δ 8.61 (d, J=4.8, 4H), 8.25 (dd, J=8.0, 1.7, 2H), 8.17 (d, J=1.6, 2H), 8.07 (d, J=7.8, 2H), 7.77 (d, J=7.6, 2H), 7.63-7.49 (m, 10H), 7.50 (d, J=8.0, 2H), 7.41 (td, J=7.5, 1.0, 2H), 7.31 (td, J=7.6, 1.1, 2H), 7.02 (t, J=4.8, 2H); TLC R$_f$ 0.30 (ethyl acetate/hexanes, 4/1); HR-MS (ESI) Anal. Calcd for $C_{48}H_{30}N_6$: 600.2532. found: 690.2535.

Moreover, the data of glass transition temperature ($T_g$), decomposition temperature ($T_d$), the longest peak wavelength value of absorption spectrum ($\lambda_{max}$), and the longest peak wavelength value of photoluminescence spectrum (PL_$\lambda_{max}$) of the aforesaid embodiments are measured and recorded in the following Table (1). From the Table (1), it is able to know that these spirally configured cis-stilbene/fluorene hybrid materials proposed by the present invention have glass transition temperatures ($T_g$) ranged from 154° C. to 194° C. and decomposition temperatures ($T_d$) ranged from 426° C. to 443° C. That means these spirally configured cis-stilbene/fluorene hybrid materials possess excellent thermal stability, and are not easy to decompose under high voltage and high current density operation conditions.

TABLE (1)

| Group n = 1 | $T_g$ (° C.) | $T_d$ (° C.) | $\lambda_{max}$ (nm) | PL $\lambda_{max}$ (nm) |
|---|---|---|---|---|
| Embodiment 1 (CNΦBSΦCN) | 194 | 435 | 365 | 430 |
| Embodiment 2 (PyBSPy) | 175 | 443 | 376 | 413 |
| Embodiment 3 (PmBSPm) | 154 | 426 | 365 | 427 |
| Embodiment 4 (ΦPm'BSPm'Φ) | 176 | 430 | 383 | 425 |

$\lambda_{max}$ and PL$\lambda_{max}$ is measured according to the following method and conditions. Absorption spectra (10 μM in CH$_2$Cl$_2$) were measured on a SP-8001 Diode Array spectrometer using spectrophotometric grade solvents. Emission spectra (10 μM) were measured on a FP-6500 luminescence spectrometer upon excitation at the absorption maxima in the same solvent. Cyclic Voltammetry (CV) measurements were carried out in 1.0 mM of substrate in anhydrous degassed solvents containing 0.1 M tetrabutylammonium perchlorate or phosphate (Bu$_4$N$^+$ClO$_4^-$ or (Bu$_4$N$^+$PF$_6^-$) as a supporting electrolyte on a Chinstruments CH1604A potentiostat. Platinum wire electrode was used as a counter electrode and glassy carbon electrode was used as a working electrode and Ag/AgCl as a reference electrode.

The steady-state photophysical measurements were conducted according to the following method and conditions. Absorption spectra were measured on an HP-8453 Diode Array spectrometer by using spectrophotometric grade CH$_2$Cl$_2$. Emission spectra (in 10 μM) were measured on an Aminco-Bowman Series 2 luminescence spectrometer upon excitation at the absorption maxima of the longest absorption band in the same solvent. The emission spectra measured in CH$_2$Cl$_2$ (10 μM) were normalized by their emission maxima to the same intensity (maximum intensity 1). Fluorescence quantum yield ($\Phi_f$ %) calculation were integrated emission area of the fluorescent spectra and compared the value to the same area measured for Coumarin 1[2c] ($\Phi_f$=0.90, CH$_2$Cl$_2$) or Coumarin 6 ($\Phi_f$=0.78, EtOH) in CH$_2$Cl$_2$ (in 10 μM). The quantum yields are calculated by using the equation 1. Where A stands for area of fluorescent emission for sample and Coumarin 1 or Coumarin 6; a is absorbance for sample and Coumarin 1 or Coumarin 6; and n is the refractive indices of solvent for sample and Coumarin 1 or Coumarin 6 (the refractive index (n) for CH$_2$Cl$_2$=1.42[2b]; for EtOH=1.36[2d]).

$$\Phi^{sample}_f = (A_{sample}/A_{standard}) \times (a_{standard}/a_{sample}) \times (n_{sample}/n_{standard})^2 \times \Phi_{standard}^f \quad (1)^{2c}$$

Moreover, the oxidation potential and the redox potential of the embodiments of these diphenylimidazole-fused, spirally configured cis-stilbene/fluorene hybrid materials can be measured by way of cyclic voltammetry (CV); therefore, the highest occupied molecular orbital energy level ($E_{HOMO}$) and lowest unoccupied molecular orbital energy level ($E_{LUMO}$) of the embodiments 1-4 of these diphenylimidazole-fused, spirally configured cis-stilbene/fluorene hybrid materials can also be calculated based on the measured oxidation potential ($E_{1/2}^{ox}$) and the redox potential ($E_{1/2}^{red}$). With reference to following Table (2), $E_{1/2}^{ox}$, $E_{1/2}^{red}$, $E_{HOMO}$, and $E_{LUMO}$ of the spirally configured cis-stilbene/fluorene hybrid materials are recorded. From the Table (2), the persons skilled in OLED material art are able to know that these diphenylimidazole-fused, spirally configured cis-stilbene/fluorene hybrid materials proposed by the present invention have the $E_{HOMO}$ ranged from 5.65 eV to 5.78 eV and the $E_{LUMO}$ ranged from 2.56 eV to 2.67 eV. Moreover, these diphenylimidazole-fused, spirally configured cis-stilbene/fluorene hybrid materials also have the oxidation potentials ranged from 0.85 V to 0.95 V and the redox potentials ranged from −2.01 V to −2.24 V.

TABLE (2)

| Group | $E_{1/2}^{ox}$ (V) | $E_{1/2}^{red}$ (V) | $E_g$ (eV) | $E_{HOMO}$ (eV) | $E_{LUMO}$ (eV) |
|---|---|---|---|---|---|
| Embodiment 1 (CNΦBSΦCN) | 0.85 | −2.24 | 3.03 | 5.65 | 2.66 |
| Embodiment 2 (PyBSPy) | 0.95 | −2.15 | 3.12 | 5.73 | 2.61 |
| Embodiment 3 (PmBSPm) | 0.89 | −2.01 | 3.13 | 5.69 | 2.56 |
| Embodiment 4 (ΦPm'BSPm'Φ) | 0.93 | −2.08 | 3.11 | 5.78 | 2.67 |

The cyclic voltammetry (CV) measurements were conducted according to the following method and conditions. CV experiments were carried out with 1.0 mM of one substrate in a given anhydrous, degassed solvent containing 0.1 M tetrabutylammonium perchlorate (n-Bu$_4$NClO$_4$) as a supporting electrolyte on a Chinstruments CH1604A potentiostat. A platinum wire electrode was used as a counter electrode, and a glassy carbon electrode was used as a working electrode. Ag/AgCl was used as a reference electrode.

The differential scanning calorimetry (DSC) analyses were conducted according to the following method and conditions. DSC measurements were performed on a SEIKO SSC 5200 DSC Computer/Thermal Analyzer. The samples were first heated (20° C./min) to melt and then quenched with liquid nitrogen. Glass transition temperatures ($T_g$) were recorded by heating (10° C./min) the cooled samples.

The thermogravimetric analyses (TGA) were conducted according to the following method and conditions. TGA measurements were performed on a SEIKO TG/DTA200 instrument by the Northern Instrument Center of Taiwan. Melting points were measured on a Hargo MP-2D instrument.

In order to prove that these proposed diphenylimidazole-fused, spirally configured cis-stilbene/fluorene hybrid materials can indeed be applied in OLEDs for being as a hole-blocking type electron transport layer, a plurality of OLED devices for control groups and experiment groups have been designed and manufactured, wherein the constituting layers for the OLED devices are integrated in the following Table (3).

TABLE (3)

| Device Group | Substrate | bottom electrode | electron transport layer | hole blocking layer | Light emitting layer | Hole transport layer | top electrode |
|---|---|---|---|---|---|---|---|
| Experiment 1 | Al | LiF | CNΦBSΦCN | CNΦBSΦCN | green phosphorescent | TAPC | HIL/ITO |
| Experiment 2 | Al | LiF | PyBSPy | PyBSPy | green phosphorescent | TAPC | HIL/ITO |
| Experiment 3 | Al | LiF | PmBSPm | PmBSPm | green phosphorescent | TAPC | HIL/ITO |
| Experiment 4 | Al | LiF | ΦPm'BSPm'Φ | ΦPm'BSPm'Φ | green phosphorescent | TAPC | HIL/ITO |
| Control 1A | Al | LiF | BmPyPb | BmPyPb | green phosphorescent | TAPC | HIL/ITO |
| Control 1B | Al | LiF | DPyPA | DPyPA | green phosphorescent | TAPC | HIL/ITO |
| Control 1C | Al | LiF | TPBi | TPBi | green phosphorescent | TAPC | HIL/ITO |
| Experiment 5 | Al | LiF | CNΦBSΦCN | CNΦBSΦCN | green phosphorescent | NPB/HT01 | HIL/ITO |
| Experiment 6 | Al | LiF | PmBSPm | PmBSPm | green phosphorescent | NPB/HT01 | HIL/ITO |
| Control 2 | Al | LiF | BmPyPb | BmPyPb | green phosphorescent | NPB/HT01 | HIL/ITO |
| Control 3 | Al | LiF | ET01 | ET01 | green phosphorescent | NPB/HT01 | HIL/ITO |

In the Table (3), 1,4,5,8,9,11-Hexaazatriphenylene-hexacarbonitrile (HATCN) is used as the HIL; 4,4'-Cyclohexylidenebis [N,N-bis(4-methylphenyl)benzenamine] (TAPC) is used as the HT01. BmPyPb is the abbreviation of 1,3-bis (3,5-dipyrid-3-yl-phenyl)benzene, DPyPA is the abbreviation of 9,10-bis(3-(pyridin-3-yl)phenyl)anthracene, and TPBi is the abbreviation of 1,3,5-Tris(1-phenyl-1H-benzimidazol-2-yl)benzene. In addition, ET01 is represented by following chemical formula 2" and the green phosphorescent dopant is Ir(ppy)$_3$ along with 11-(4,6-diphenyl-1,3,5-triazin-2-yl)-12-phenyl-11,12-dihydroindolo[2,3-a]carbazole as the host which is represented by the following chemical formula (V).

[chemical formula 2"]

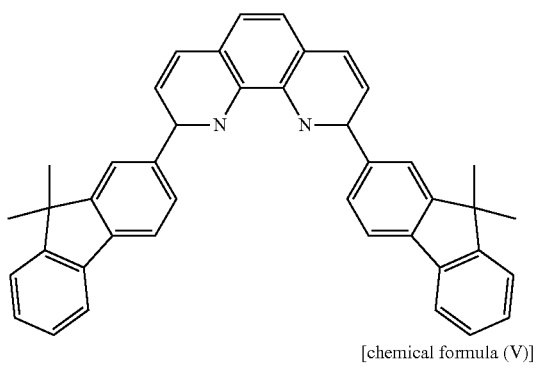

[chemical formula (V)]

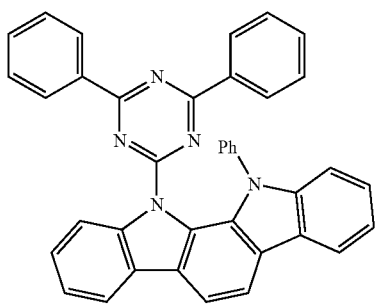

The devices were fabricated and measured according to the following method and conditions. All the materials were either commercially available or synthesized as described in the experimental section and were subjected to gradient sublimation under high vacuum prior to use. The substrate was an indium tin oxide (ITO) coated glass with a sheer resistance of ~30Ω/□. Prepatterned ITO substrates were cleaned sequentially by sonication in a detergent solution, doubly distilled water, and EtOH for 5 min in turn before being blown dry with a stream of nitrogen. The ITO substrate was then treated with oxygen plasma for 5 min before being loaded into the vacuum chamber. The organic layers were deposited thermally at a rate of 0.1-0.3 nm/s in a chamber (ULVAC, TU-12RE) under a pressure of 5×10$^{-6}$ Torr. Devices were constructed with a 40 nm thickness of α-NPB as the hole transporting layer (HTL), 40 nm of emitter as the light-emitting layer (LEL), 40 nm of Alq$_3$, TPBI, or our claimed ETs as the electron-transporting layer (ETL) and the hole-blocking layer (HBL), 1 nm of LiF as the electron-injecting layer (EIL), and 150 nm of Al as the cathode, respectively. Current-voltage-light intensity (I-V-L) characteristics and EL spectra were measured and recorded by PRECISE GAUGE, EL-1003.

It is able to know that the materials of TPBi, DPyPA, BmPyPb, and ET01 recorded in the Table (3) are also used as OLED device's electron transport layers. Continuously, the turn-on voltage ($V_{on}$), the external quantum efficiency ($\eta_{ext}$), the current efficiency ($\eta_c$), the power efficiency ($\eta_p$), and the maximum luminance ($L_{max}$) of the OLED devices have been measured and recorded in the following Table (4).

TABLE (4)

| Device Group | $\lambda_{max}$ (nm) | $V_{on}$ (V) | $\eta_{ext}$ (%) | $\eta_c/\eta_p$ (%) | $L_{max}$ (cd/m$_2$) |
|---|---|---|---|---|---|
| Experiment 1 | 516 | 2.5 | 17.6 | 47.3/48.5 | 104,200 |
| Experiment 2 | 516 | 2.3 | 17.7 | 44.5/52.7 | 117,075 |
| Experiment 3 | 516 | 2.2 | 12.8 | 38.7/46.9 | 93,800 |
| Experiment 4 | 516 | 2.1 | 19.4 | 42.2/50.5 | 120,106 |
| Control 1A | 516 | 2.5 | 6.3 | 22.8/18.0 | 142,100 |

TABLE (4)-continued

| Device Group | $\lambda_{max}$ (nm) | $V_{on}$ (V) | $\eta_{ext}$ (%) | $\eta_c/\eta_p$ (%) | $L_{max}$ (cd/m$_2$) |
|---|---|---|---|---|---|
| Control 1B | 516 | 3.0 | 10.2 | 37.8/24.0 | 40,700 |
| Control 1C | 516 | 3.0 | 6.9 | 24.7/22.0 | 37,640 |
| Experiment 5 | 516 | 4.7 | 12.9 | 33.8/19.8 | 76,930 |
| Experiment 6 | 516 | 4.7 | 13.6 | 36.2/20.1 | 54,900 |
| Control 2 | 516 | 4.5 | 10.8 | 36.8/25.7 | 42,150 |
| Control 3 | 516 | 5.5 | 7.84 | 27.6/15.8 | 17,700 |

With reference to the measured data of the green phosphorescent OLED devices in the Table (4), one can find that the OLED devices using single hole transport layer of Experiments 1-4 show excellent $\eta_{ext}$, $\eta_c$, $\eta_p$, and $L_{max}$ and are much superior to the OLED devices using single hole transport layer of Control 1A, Control 1B, and Control 1C. Among them, experiments 1 (CNΦBSΦCN) and 3 (PmB-SPm) show the best results, where the $\eta_{ext}$ are in a range of 12.8-17.6%, $\eta_c$ are in a range of 38.7-47.3 cd/A, $\eta_p$ are in a range of 46.9-48.5 lm/w, and $L_{max}$ are in a range of 93,800-104,200 cd/m$^2$.

In addition, the measured data also reveal that the OLED devices using single hole-transport layer of Experiment 3 and Experiment 4 show excellent $\eta_{ext}$, $\eta_c$, $\eta_p$, and $L_{max}$ and are superior to the OLED devices using complex (i.e., double) hole transport layer of Control 2 and Control 3. Moreover, the commercial OLED device using complex (double) hole transport layer of Experiment 6 (PmBSPm) also shows excellent $\eta_{ext}$, $\eta_c$, $\eta_p$, and $L_{max}$, which is superior to the OLED devices using complex (i.e., double) hole transport layer of Control 2 and Control 3.

Furthermore, device life time evaluation test for the green phosphorescent OLEDs have also been completed based on a starting luminance of 10,000 cd/cm$^2$. Life time evaluation test results reveal that the decay half lifetimes (LT$_{50}$) of the green phosphorescent OLED for Experiment 5 and 6 are 11,620 and 12,630 hours, respectively. In addition, the decay half lifetime (LT$_{50}$) for the green phosphorescent OLEDs of Control 1A and Control 3 are respectively measured as 1,000 hours and 13,500 hours. Moreover, after replacing the BmPyPb in the green phosphorescent OLEDs of Control 1A by the TmPyPb, the green phosphorescent OLEDs having the TmPyPb material is measured with the LT$_{50}$ of only 210 hours.

Therefore, through above descriptions, these diphenylimidazole-fused, spirally configured cis-stilbene/fluorene hybrid materials for OLEDs proposed by the present invention have been introduced completely and clearly; in summary, the present invention includes the advantages of:

(1) The diphenylimidazole-fused, spirally configured cis-stilbene/fluorene hybrid materials are diphenylimidazole-fused, spirally-configured cis-stilbene/fluorene derivatives bearing cayanoaryl and cyanoheteroaryl substituents having glass transition temperatures ranged from 154° C. to 194° C., decomposition temperatures ranged from 426° C. to 443° C., reversible electron transport property, and balanced charges motilities.

(2) Moreover, a variety of experimental data have proved that these diphenylimidazole-fused, spirally configured cis-stilbene/fluorene hybrid materials can indeed be used as a hole-blocking type electron-transporter for OLEDs; moreover, the experimental data also reveal that the OLEDs using these diphenylimidazole-fused, spirally configured cis-stilbene/fluorene hybrid materials can indeed be used as the hole-blocking type electron-transporter are able to show excellent external quantum efficiency ($\eta_{ext}$), current efficiency ($\eta_c$), power efficiency ($\eta_p$), maximum luminance ($L_{max}$), and device lifetime performances better than the conventional or commercial OLEDs.

Figure 2:
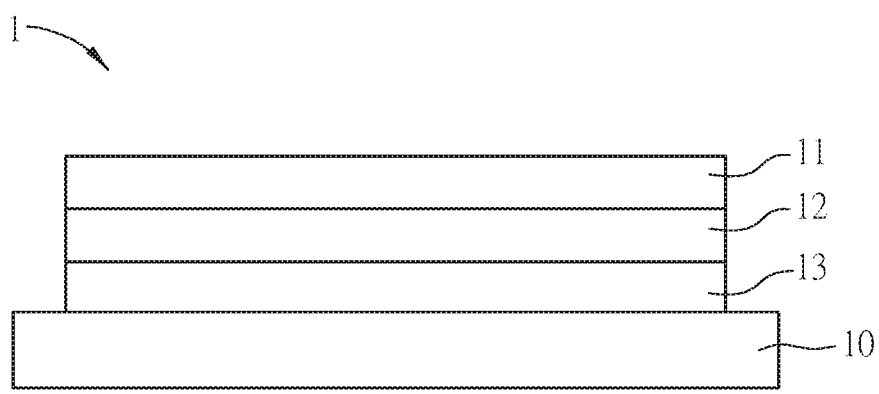
FIG. 2 is a schematic diagram of the optoelectronic device according to a preferred embodiment of the present invention.

The present invention also provides another preferred embodiment which is an optoelectronic device. As shown in FIG. 2, the optoelectronic device 1 comprises a first electrode 11, an interlayer 12 and a second electrode 13 sequentially disposed on a substrate 10. The interlayer has a compound substantially the same as described in the above-mentioned preferred embodiment of the present application. The compound comprises a seven-membered ring portion and an imidazole fragment. The seven-membered ring portion is composed of a cis-stilbene fragment and a tetrahedral coordination bridging atom fragment, and the imidazole fragment is connected to the cis-stilbene fragment. The detail of the compounds, such as the feasible preferred substituents and electrical characteristics, can refer to the previous embodiments, and they are not repeated here.

In addition, the optoelectronic device 1 is an organic light emitting device (OLED), the interlayer 12 is an electron transport layer, a hole blocking layer and/or a light emitting layer. Moreover, the optoelectronic device 1 of the present preferred embodiment can be applied to an organic light emitting device, an organic solar cell device, an organic thin film transistor, an organic photodetector, a flat panel display, a computer monitor, a television, a billboard, a light for interior or exterior illumination, a light for interior or exterior signaling, a heads up display, a fully transparent display, a flexible display, a laser printer, a telephone, a cell phone, a tablet computer, a laptop computer, a digital camera, a camcorder, a viewfinder, a micro-display, a vehicle, a large area wall, a theater or stadium screen, or a sign.

Another objective of the present invention is to provide a process for the synthesis of a compound of chemical formula B. The process comprises the following step: reacting a compound of chemical formula B-1 and a compound of chemical formula B-2 to produce the compound of chemical formula B.

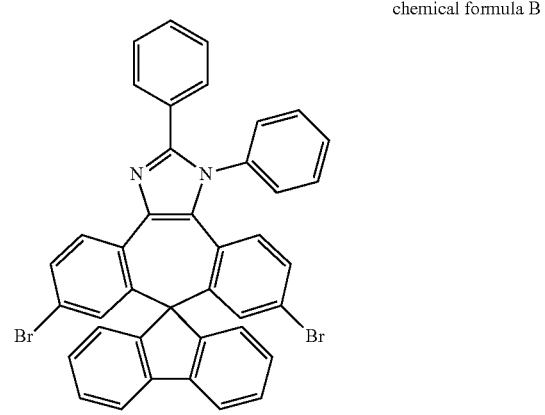

chemical formula B

-continued chemical formula B-1

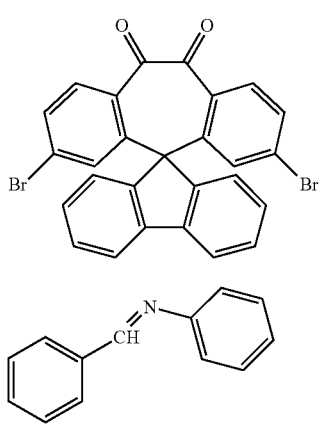

chemical formula B-2

The features of the diphenylimidazole-fused, spirally configured cis-stilbene/fluorene hybrid compounds, the optoelectronic devices and the process for the synthesis of such compounds according to the above embodiments will become more fully understood by the person who skilled in the art from the following experimental examples which further illustrate the physical and chemical properties thereof.

Example A

Synthetic Scheme I

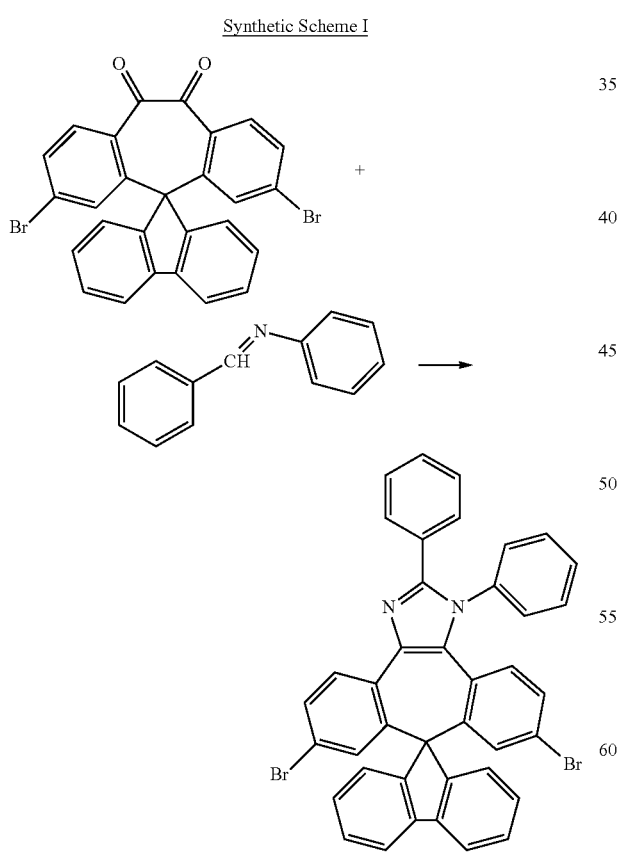

A 100 ml two-necked, round-bottom flask with a stirrer is mount to a reflux tube and then the reflux system was open. After vacuum drying, the nitrogen gas was introduced into the flask. According to Synthetic Scheme I, compound of chemical formula B-1 1594 mg (3 mmole), compound of chemical formula B-2 815.1 mg (4.5 mmole) and ammonium acetate ($NH_4OAc$) 3004.9 mg (39 mmole) were added into the flask, followed by injecting with 15 ml acetic acid and stirring with the stirrer. The flask was then put in an oil-bath of 70° C. for 30 hours. After checking that no starting materials exist in the reaction mixture by thin-layer chromatography, the flask is pulled up for cooling down. The reflux tube is then dismount and the flask is wiped with n-hexane to remove the remaining silica oil from the outer wall of the flask. The reaction mixture was extracted with water and dichloromethane (three times). Organic layer was separated and was dried with $MgSO_4$, followed by filtering and removing the solvent by a rotary evaporator. The crude residue was purified by column chromatography on silica gel (EtOAc/n-hexane, 1:8). The crude solid was re-crystallized from $CH_2Cl_2$/n-hexane to afford 1165 mg of pure compound of chemical formula B (yield 80%).

Accordingly, as to the series of diphenylimidazole-fused, spirally configured cis-stilbene/fluorene hybrid compounds and the optoelectronic device comprising the same according to the disclosure, the compounds bear cyanoaryl and cyano-heteroaryl subunits, and are diphenylimidazole-fused, spirally-configured cis-stilbene/fluorene derivatives having glass transition temperatures ranged from 154° C. to 194° C., decomposition temperatures ranged from 426° C. to 443° C., reversible electron transport property, and balanced charges motilities. In addition, a variety of experimental data have proved that these diphenylimidazole-fused, spirally configured cis-stilbene/fluorene hybrid materials can indeed be used as hole-blocking type, electron-transporters and emitting materials for OLEDs. Moreover, the experimental data also reveal that the OLEDs using these diphenylimidazole-fused, spirally configured cis-stilbene/fluorene hybrid materials can indeed be used as the hole-blocking type electron-transporters and are able to show excellent external quantum efficiency ($\eta_{ext}$), current efficiency ($\eta_c$), power efficiency ($\eta_p$), maximum luminance ($L_{max}$), and device lifetime better than those of phosphorescent OLEDs based on the conventional or commercial electron transport materials.

Although the present invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the present invention.

What is claimed is:

1. A compound represented by general formula I:

(general formula I)

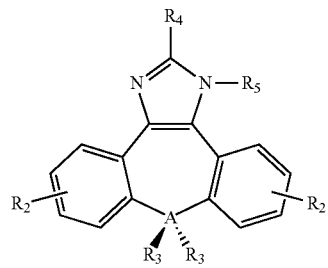

wherein A is carbon atom or silicon atom;

wherein $R_2$ is an electron-withdrawing group which is independently a phosphine oxide group, aromatic ring group, or heteroaromatic ring group optionally substituted by one or more radicals Y;

wherein $R_4$ and $R_5$ are identical or different and each of $R_4$ and $R_5$ is independently an aromatic ring group, heteroaromatic ring group, alkyl group or alkenyl group optionally substituted by one or more radicals Y;

wherein radical Y is identical or different on each occurrence and is a hydrogen atom, halogen atom, cyano group, trifluoromethyl group, phosphine oxide group, alkyl group, alkenyl group, aromatic ring group or heteroaromatic ring group optionally substituted by one or more radicals Y';

wherein radical Y' is identical or different on each occurrence and is a hydrogen atom, cyano group, aromatic ring group, heteroaromatic ring group, alkyl group or alkenyl group;

wherein $R_3$ is independently a methyl group, phenyl group, tert-butyl group or two of $R_3$ are linked by a single bond represented by general formula I-2,

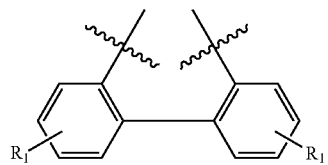

(general formula I-2)

wherein $R_1$ is a hydrogen atom, tert-butyl group or naphthyl group.

2. The compound of claim 1, which is applied in an organic light emitting device (OLED) for being as hole-blocking materials, and/or electron-transporting materials.

3. The compound of claim 1, wherein the aromatic ring group or heteroaromatic ring group in $R_2$, $R_4$, $R_5$, Y or Y' is independently a fused aryl group or heteroaryl group.

4. The compound of claim 1, wherein the aromatic ring group or heteroaromatic ring group in $R_2$, $R_4$, $R_5$ or Y is independently a phenyl group, 1-naphthyl group, 2-naphthyl group, thiophenyl group, pyrimidinyl group, pyrrolyl group, quinolinyl group, triazinyl group, pyridyl group or benzimidazolyl group.

5. The compound of claim 1, wherein the aromatic ring group or heteroaromatic ring group in $R_2$, $R_4$, $R_5$ or Y' is independently an imidazolyl group, phenyl group, pyridyl group, 1H-pyrrolo[2,3-b]pyridine group or carbazolyl group.

6. The compound of claim 1, wherein the alkyl group or alkenyl group in $R_4$, $R_5$, Y or Y' is independently a straight-chain alkyl group or alkenyl group, a branched alkyl group or alkenyl group, or a cyclic alkyl group or alkenyl group.

7. The compound of claim 1, wherein $R_2$ is independently selected from the groups of general formula II-1-2 to general formula II-1-56, and wherein n is 1 or 2

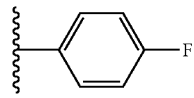

general formula II-1-2

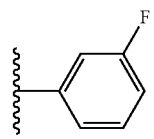

general formula II-1-3

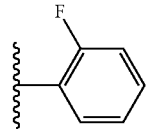

general formula II-1-4

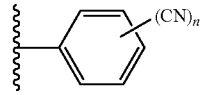

general formula II-1-5

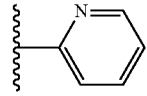

general formula II-1-6

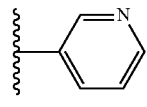

general formula II-1-7 general formula II-1-8

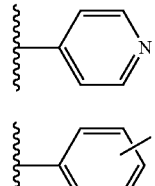

general formula II-1-9

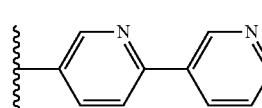

general formula II-1-10

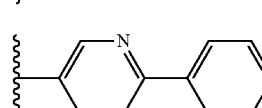

general formula II-1-11

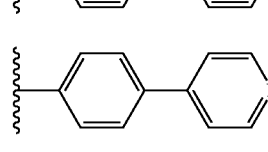

general formula II-1-12 general formula II-1-13

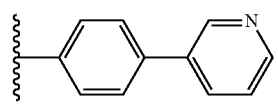

general formula II-1-14

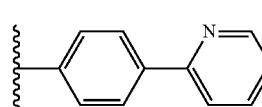

general formula II-1-15

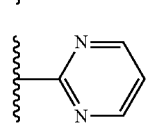

general formula II-1-16

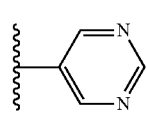

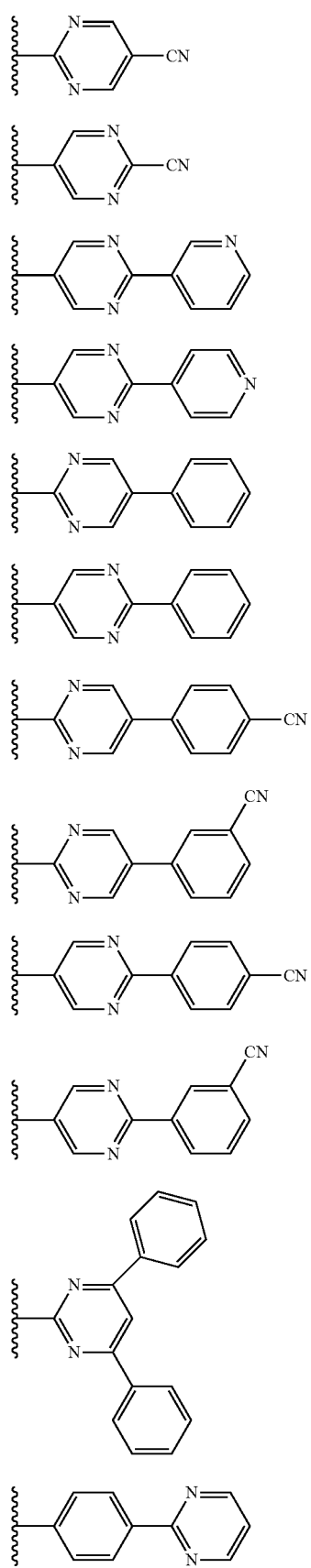
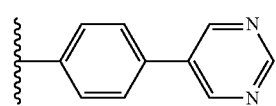
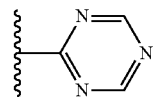
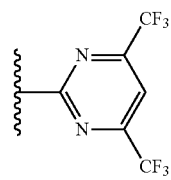
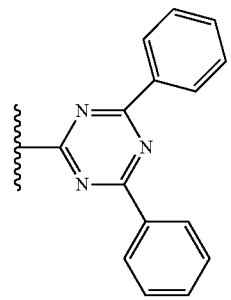
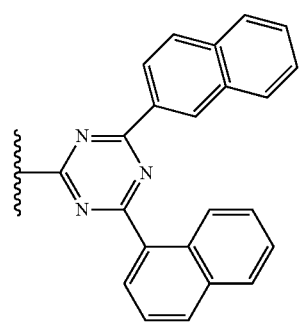
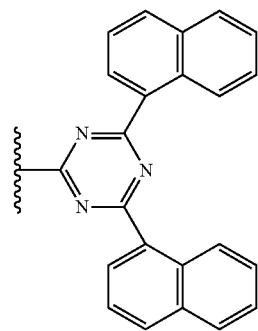
general formula II-1-17
general formula II-1-18
general formula II-1-19
general formula II-1-20
general formula II-1-21
general formula II-1-22
general formula II-1-23
general formula II-1-24
general formula II-1-25
general formula II-1-26
general formula II-1-27
general formula II-1-28
general formula II-1-29
general formula II-1-30
general formula II-1-31
general formula II-1-32
general formula II-1-33
general formula II-1-34 general formula II-1-35
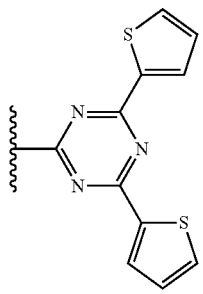
general formula II-1-36
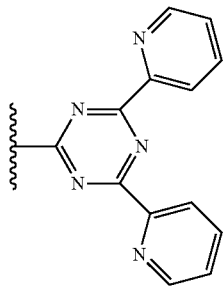
general formula II-1-37
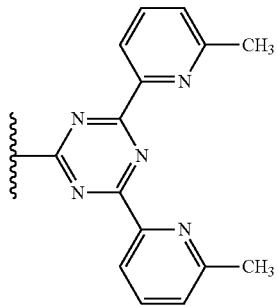
general formula II-1-38
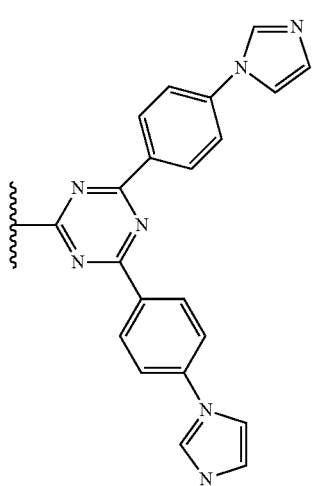
general formula II-1-39
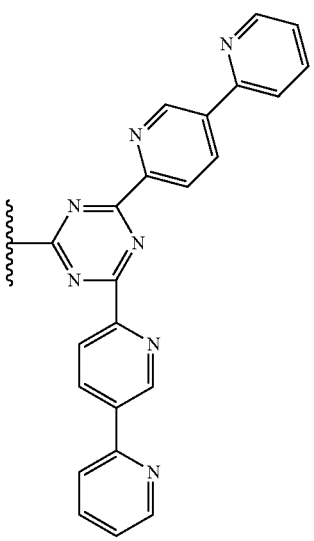
general formula II-1-40
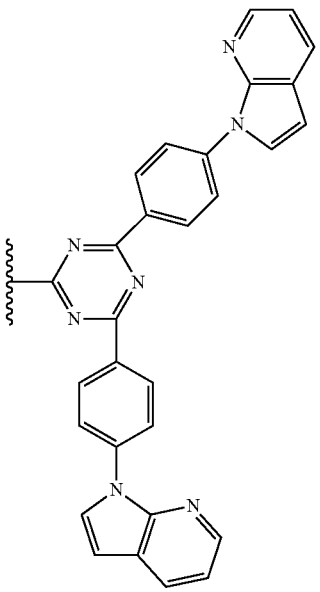
general formula II-1-41
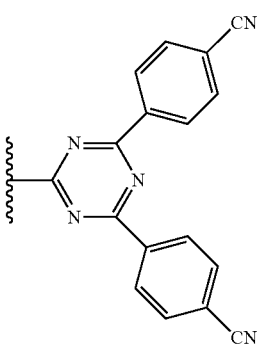

general formula II-1-42
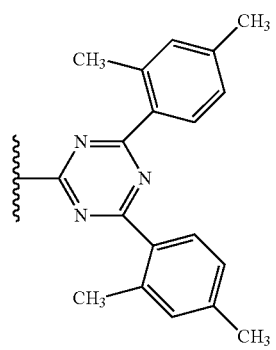
general formula II-1-43
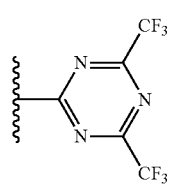
general formula II-1-44
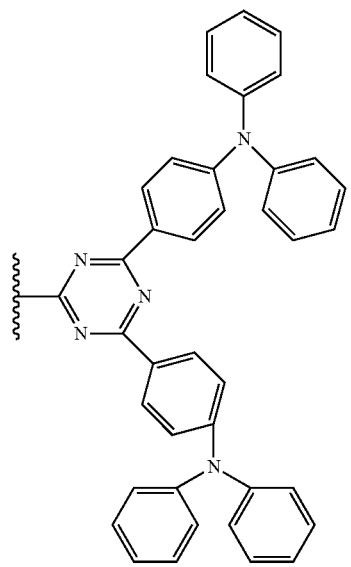
general formula II-1-45
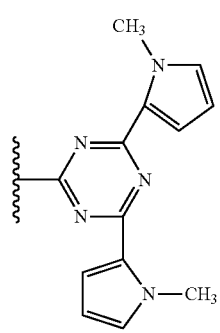
general formula II-1-46
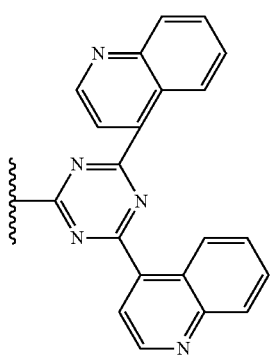
general formula II-1-47
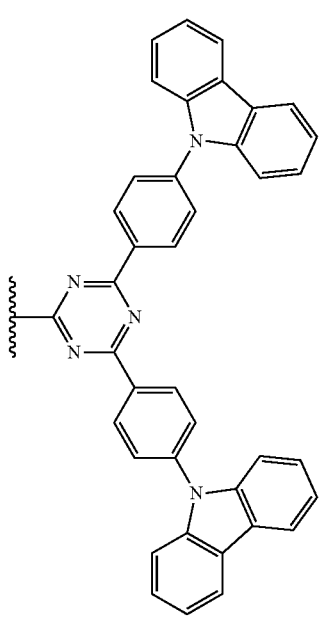
general formula II-1-48
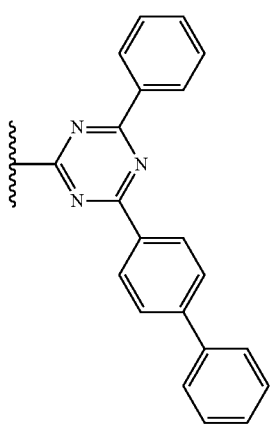

general formula II-1-49

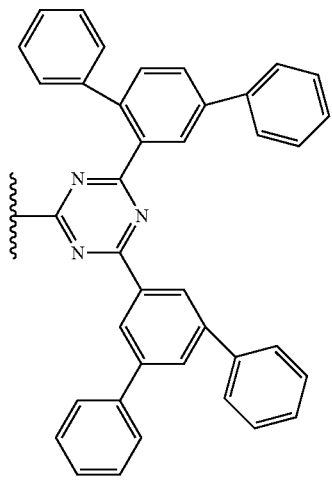

general formula II-1-50

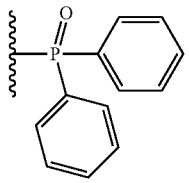

general formula II-1-51

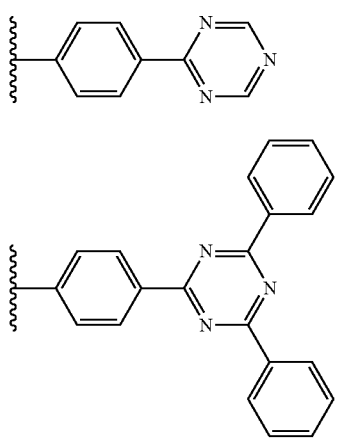

general formula II-1-52

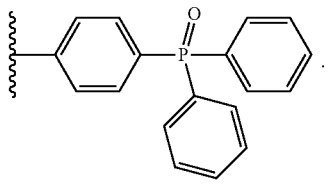

general formula II-1-53

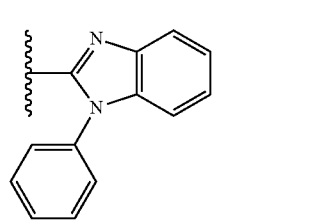

general formula II-1-54

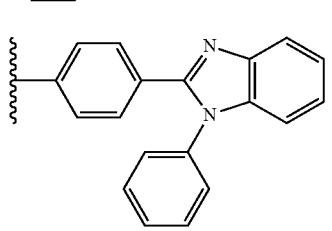

general formula II-1-55

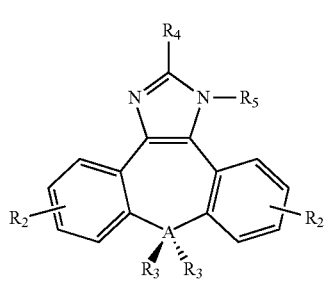

general formula II-1-56

8. An optoelectronic device comprising a first electrode, an interlayer and a second electrode sequentially disposed on a substrate, wherein the interlayer has a compound, the compound represented by general formula I:

(general formula I)

wherein A is carbon atom or silicon atom;

wherein $R_2$ is an electron-withdrawing group which is independently a phosphine oxide group, aromatic ring group, or heteroaromatic ring group optionally substituted by one or more radicals Y;

wherein $R_4$ and $R_5$ are identical or different and each of $R_4$ and $R_5$ is independently an aromatic ring group, heteroaromatic ring group, alkyl group or alkenyl group optionally substituted by one or more radicals Y;

wherein radical Y is identical or different on each occurrence and is a hydrogen atom, halogen atom, cyano group, trifluoromethyl group, phosphine oxide group, alkyl group, alkenyl group, aromatic ring group or heteroaromatic ring group optionally substituted by one or more radicals Y';

wherein radical Y' is identical or different on each occurrence and is a hydrogen atom, cyano group, aromatic ring group, heteroaromatic ring group, alkyl group or alkenyl group;

wherein $R_3$ is independently a methyl group, phenyl group, tert-butyl group or two of $R_3$ are linked by a single bond represented by general formula I-2, (general formula I-2)

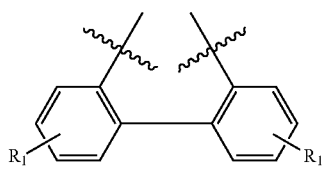

wherein $R_1$ is a hydrogen atom, tert-butyl group or naphthyl group.

9. The optoelectronic device of claim 8, wherein the aromatic ring group or heteroaromatic ring group in $R_2$, $R_4$, $R_5$, Y or Y' is independently a fused aryl group or heteroaryl group.

10. The optoelectronic device of claim 8, wherein the aromatic ring group or heteroaromatic ring group in $R_2$, $R_4$, $R_5$ or Y is independently a phenyl group, 1-naphthyl group, 2-naphthyl group, thiophenyl group, pyrimidinyl group, pyrrolyl group, quinolinyl group, triazinyl group, pyridyl group or benzimidazolyl group.

11. The optoelectronic device of claim 8, wherein the aromatic ring group or heteroaromatic ring group in $R_2$, $R_4$, $R_5$ or Y' is independently an imidazolyl group, phenyl group, pyridyl group, 1H-pyrrolo[2,3-b]pyridine group or carbazolyl group.

12. The optoelectronic device of claim 8, wherein the alkyl group or alkenyl group in $R_4$, $R_5$, Y or Y' is independently a straight-chain alkyl group or alkenyl group, a branched alkyl group or alkenyl group, or a cyclic alkyl group or alkenyl group.

13. The optoelectronic device of claim 8, wherein $R_2$ is independently selected from the groups of general formula II-1-2 to general formula II-1-56, and wherein n is 1 or 2 general formula II-1-2

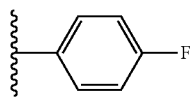

general formula II-1-3

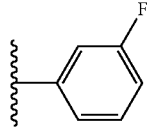

general formula II-1-4

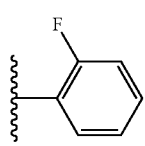

general formula II-1-5

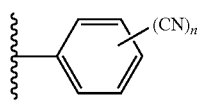

general formula II-1-1=6

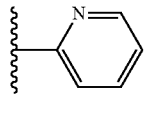

general formula II-1-7

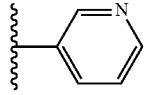

-continued general formula II-1-8

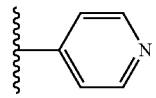

general formula II-1-9

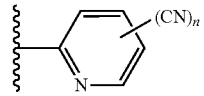

general formula II-1-10

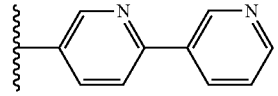

general formula II-1-11

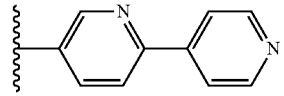

general formula II-1-12

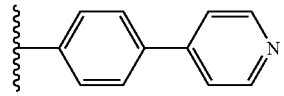

general formula II-1-13

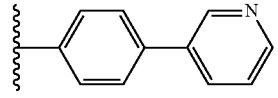

general formula II-1-14

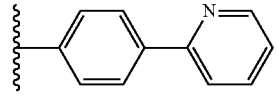

general formula II-1-15

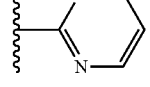

general formula II-1-16

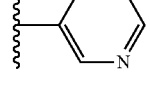

general formula II-1-17

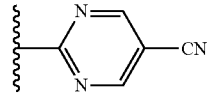

general formula II-1-18

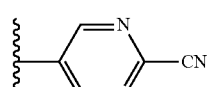

general formula II-1-19

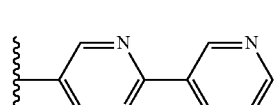

general formula II-1-20

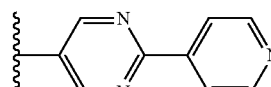

general formula II-1-21

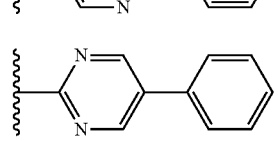

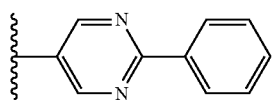 general formula II-1-22
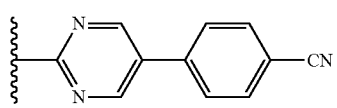 general formula II-1-23
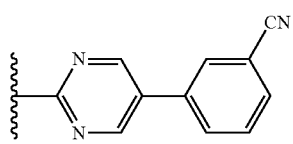 general formula II-1-24
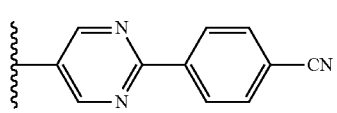 general formula II-1-25
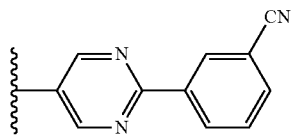 general formula II-1-26
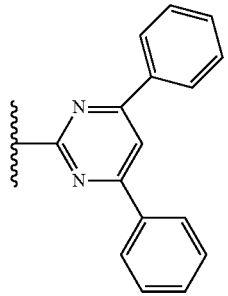 general formula II-1-27
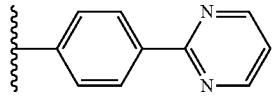 general formula II-1-28
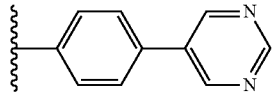 general formula II-1-29
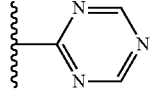 general formula II-1-30
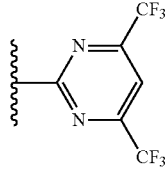 general formula II-1-31
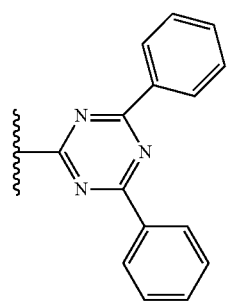 general formula II-1-32
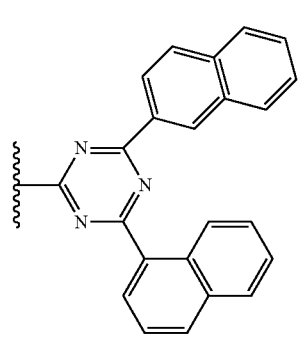 general formula II-1-33
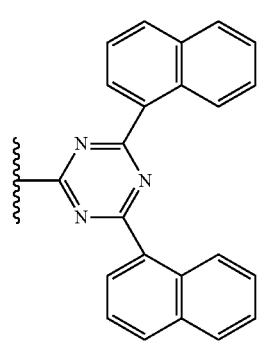 general formula II-1-34
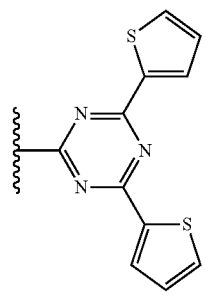 general formula II-1-35
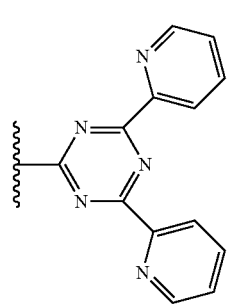 general formula II-1-36 general formula II-1-37
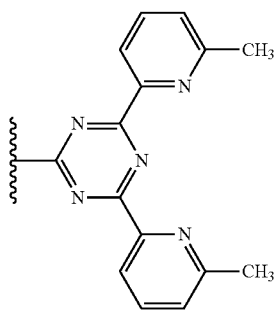
general formula II-1-38
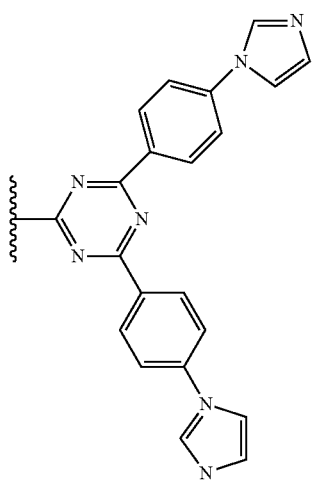
general formula II-1-39
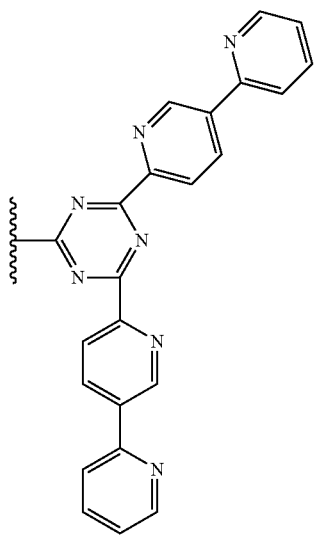
general formula II-1-40
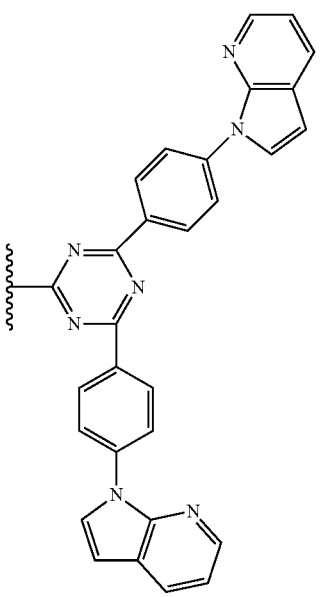
general formula II-1-41
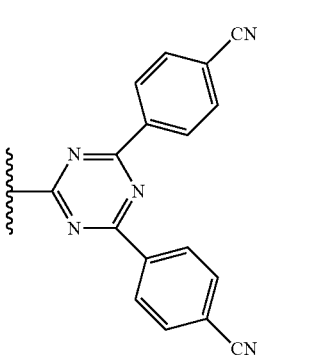
general formula II-1-42
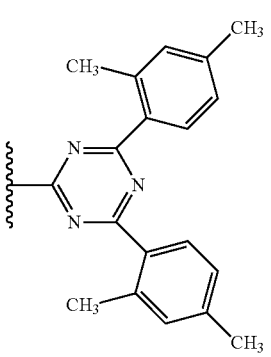
general formula II-1-43
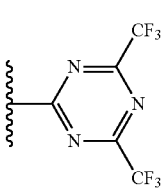

general formula II-1-44
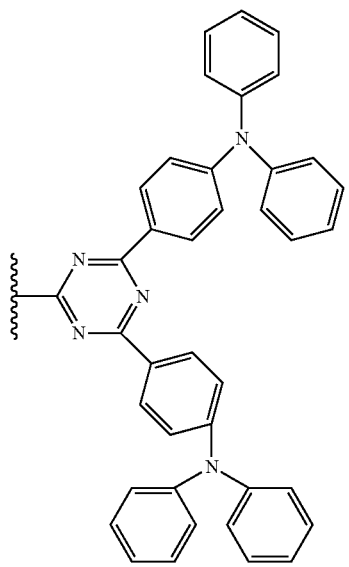
general formula II-1-45
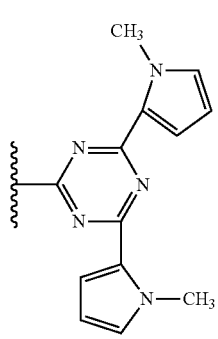
general formula II-1-46
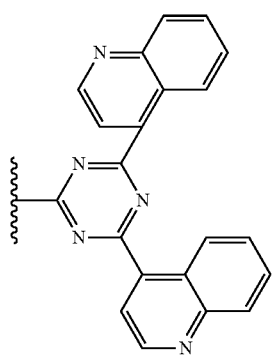
general formula II-1-47
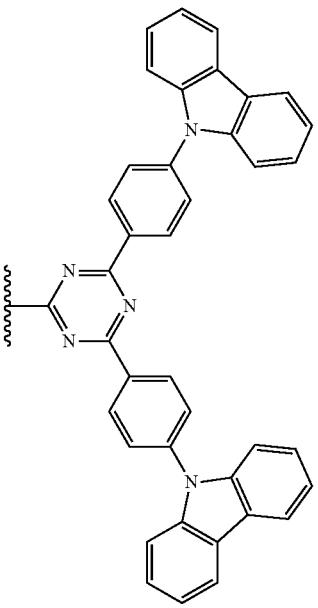
general formula II-1-48
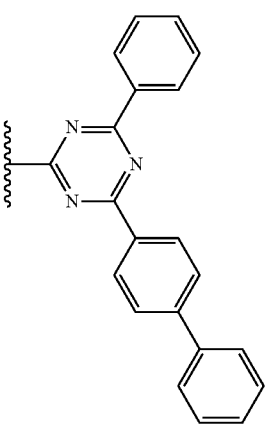
general formula II-1-49
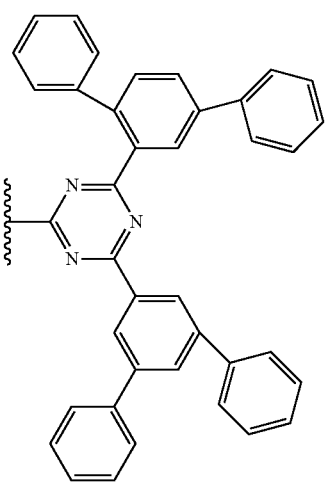
general formula II-1-50
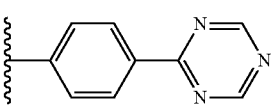

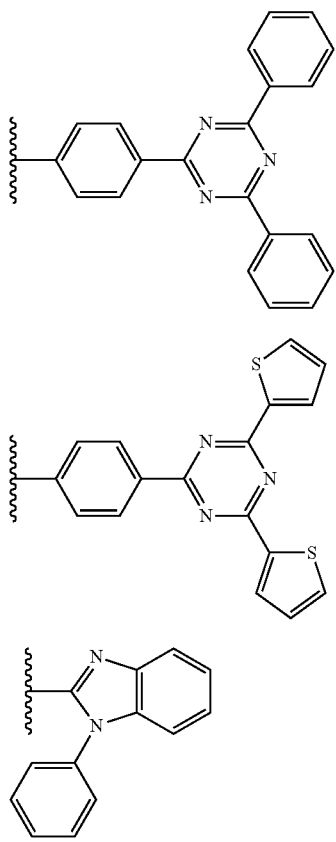
general formula II-1-51
general formula II-1-52
general formula II-1-53
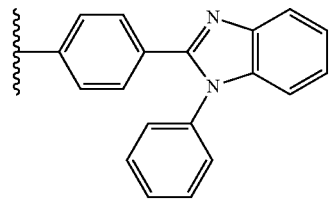
general formula II-1-54
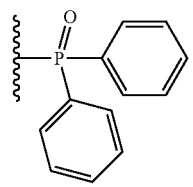
general formula II-1-55
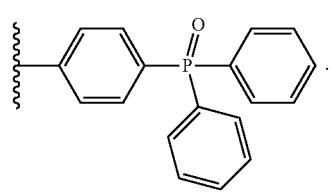
general formula II-1-56
14. The optoelectronic device of claim 8, wherein the optoelectronic device is an organic light emitting device (OLED), and the interlayer is an electron transport layer, a hole blocking layer and/or a light emitting layer.
* * * * *